(12) United States Patent
Bowman et al.

(10) Patent No.: US 8,962,709 B2
(45) Date of Patent: Feb. 24, 2015

(54) RESIN SYSTEMS FOR DENTAL RESTORATIVE MATERIALS AND METHODS USING SAME

(71) Applicant: The Regents of the University of Colorado, a body corporate, Dover, CO (US)

(72) Inventors: Christopher N. Bowman, Boulder, CO (US); Neil B. Cramer, Boulder, CO (US)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 0 days.

(21) Appl. No.: 13/735,709

(22) Filed: Jan. 7, 2013

(65) Prior Publication Data
US 2013/0123381 A1    May 16, 2013

Related U.S. Application Data

(63) Continuation-in-part of application No. 13/473,482, filed on May 16, 2012, now abandoned, which is a continuation of application No. 12/415,783, filed on Mar. 31, 2009, now Pat. No. 8,192,673, which is a continuation-in-part of application No. 10/576,635, filed as application No. PCT/US2004/034968 on Oct. 22, 2004, now Pat. No. 7,838,571.

(60) Provisional application No. 60/513,900, filed on Oct. 22, 2003.

(51) Int. Cl.
| | |
|---|---|
| A61F 2/00 | (2006.01) |
| A61K 6/02 | (2006.01) |
| A61K 6/08 | (2006.01) |
| A61K 6/087 | (2006.01) |
| A61K 6/00 | (2006.01) |
| C08J 7/12 | (2006.01) |
| C08G 75/04 | (2006.01) |
| C08F 2/48 | (2006.01) |
| C08F 2/50 | (2006.01) |
| C09D 4/00 | (2006.01) |
| C08F 222/10 | (2006.01) |

(52) U.S. Cl.
CPC . *A61K 6/00* (2013.01); *C08J 7/123* (2013.01); *C08G 75/045* (2013.01); *C08F 2/48* (2013.01); *C08F 2/50* (2013.01); *C09D 4/00* (2013.01); *C08F 222/1006* (2013.01)
USPC ............. 523/115; 523/116; 522/83; 522/118; 522/42; 522/44; 522/48; 522/66; 522/64

(58) Field of Classification Search
USPC ..................... 522/83, 180, 42, 44, 48, 64, 66; 523/115, 116; 264/494
See application file for complete search history.

(56) References Cited

U.S. PATENT DOCUMENTS 4,536,523 A * 8/1985 Antonucci .................... 523/115
5,100,929 A * 3/1992 Jochum et al. ................. 522/64

(Continued)

*Primary Examiner* — Sanza McClendon
(74) *Attorney, Agent, or Firm* — Saul Ewing LLP; Kathryn Doyle; Domingos J. Silva

(57) ABSTRACT

The invention includes a new photopolymerizable resin system for dental restorative materials. The resin system utilizes a thiol-ene component as the reactive diluent in dimethacrylate systems. The ternary resin system comprises a thiol monomer, an ene monomer and a dimethacrylate monomer. The system of the invention has enhanced overall functional group conversion, improved polymer mechanical properties, and reduced shrinkage stress of the ternary system when compared to either traditional dimethacrylate or thiol-ene resin systems.

23 Claims, 13 Drawing Sheets

(56) References Cited

U.S. PATENT DOCUMENTS

| | | | |
|---|---|---|---|
| 5,321,053 A * | 6/1994 | Hino et al. | 522/26 |
| 5,554,655 A * | 9/1996 | Thoene | 514/665 |
| 5,889,132 A * | 3/1999 | Rheinberger et al. | 526/279 |
| 6,251,963 B1 * | 6/2001 | Kohler et al. | 522/64 |
| 6,384,107 B2 * | 5/2002 | Liu | 523/118 |
| 6,479,622 B1 * | 11/2002 | Gross et al. | 528/376 |
| 6,624,211 B2 * | 9/2003 | Karim et al. | 523/116 |
| 7,659,324 B2 * | 2/2010 | Moszner et al. | 522/183 |

* cited by examiner

RESIN SYSTEMS FOR DENTAL RESTORATIVE MATERIALS AND METHODS USING SAME

CROSS-REFERENCES TO RELATED APPLICATIONS

This application is a continuation-in-part of and claims priority to U.S. application Ser. No. 13/473,482, filed May 16, 2012, which is a continuation of and claims priority to U.S. application Ser. No. 12/415,783, filed Mar. 31, 2009, now issued as U.S. Pat. No. 8,192,673, which is a continuation-in-part of and claims priority to U.S. application Ser. No. 10/576,635, filed Apr. 21, 2006, now issued as U.S. Pat. No. 7,838,571, which is 35 U.S.C. §371 national phase application from, and claiming priority to, International Application No. PCT/US04/34968, filed Oct. 22, 2004, which claims priority to U.S. Provisional Application No. 60/513,900, filed Oct. 22, 2003, all of which applications are herein incorporated by reference in their entireties.

STATEMENT REGARDING FEDERALLY SPONSORED RESEARCH OR DEVELOPMENT

This invention was made with government support under grant numbers DE010959 and DE018233 awarded by the National Institutes of Health. The government has certain rights in the invention.

BACKGROUND OF THE INVENTION

Currently, most commercial photocurable dental restorative resins are based on dimethacrylates and the reaction mechanism is through chain-growth free radical polymerization. Existing dimethacrylate systems are popular for fillings and other dental prostheses because of their esthetic merit and "cure-on-command" feature. These formulations have resulted in significant advancements in the field of dentistry.

Such dental restorative materials are often mixed with 45 to 85% by weight (wt %) silanized filler compounds such as barium, strontium, zirconia silicate and/or amorphous silica to match the color and opacity to a particular use or tooth. The filler is typically in the form of particles with a size ranging from 0.01 to 5.0 micrometers.

The photocurable restorative materials are often sold in separate syringes or single-dose capsules of different shades. If provided in a syringe, the user dispenses (by pressing a plunger or turning a screw adapted plunger on the syringe) the necessary amount of restorative material from the syringe. Then, the material is placed directly into the cavity, mold, or location of use. If provided as a single-dose capsule, the capsule is placed into a dispensing device that can dispense the material directly into the cavity, mold, and such. After the restorative material is placed, it is photopolymerized or cured by exposing the restorative material to the appropriate light source. The resulting cured polymer may then be finished or polished as necessary with appropriate tools. Such dental restoratives can be used for direct anterior and posterior restorations, core build-ups, splinting and indirect restorations including inlays, onlays and veneers.

Although easy to use, these dimethacrylate systems have several drawbacks and there are a number of properties of the resin chemistry that, if improved upon, would increase the performance, longevity and biocompatibility of composite restorations (Sakaguchi et al., 2005, Dent. Mat. 21:43-46; Dauvillier et al., 2001, J. Biomed. Mat. Res. 58(1):16-26, 2001; Dauvillier et al., 2000, J. Dent. Res. 79(3):818-823; Yourtee et al., 1997, In Vitro Tox. 10:245-251). The most significant shortcomings of methacrylate-based resins are high volumetric shrinkage (Ferracane, 2005, Dent. Mat. 21:36-42), high polymerization stress (Braga et al., 2005, Dent. Mat. 21:962-970; Lu et al., 2005, Dent. Mat., 21(12):1129-1136; Braga and Ferracane, 2002, J. Den.1 Res. 81:114-118) and low functional group conversion (Darmani and Al-Hiyasat, 2006, Dent. Mat. 22:353-358; Sasaki et al., 2005, J. Mat. Sci.: Mat. Med. 16:297-300; Pulgar et al., 2000, Envir. Health Persp. 108:21-27). The chain growth polymerization mechanism results in long chains and therefore early gelation which contributes to both volume shrinkage and shrinkage stress. The current systems typically only reach a final double bond conversion of 55 to 75%, which not only contributes to the insufficient wear resistance and mechanical properties, but also jeopardizes the biocompatibility of the composites due to the leachable unreacted monomers. Additionally, the residual monomer left in the restoration after curing is extractable and may leach out of the restoration and into the body, with unknown consequences (Sasaki et al., 2005, J. Mat. Sci.: Mat. Med. 16:297-300; Pulgar et al., 2000, Envir. Health Persp. 108:21-27). There is concern that residual monomers may cause allergic reactions and sensitization in patients (Theilig et al., 2000, J. Biomed. Mat. Res. 53(6):632-639). There is also reason to believe that release of the most common reactive diluent, triethylene glycol dimethacrylate (TEGDMA), may also contribute to local and systemic adverse effects by dental composites (Hansel et al., 1998, J. Dent. Res. 77(1):60-67; Englemann et al., 2001, J. Dent. Res. 80(3):869-875; Schweikl and Schmalz, 1999, Mut. Res.-Gen. Toxic. Envir. Mutag. 438:71-78; Darmani and Al-Hiyasat, 2006, Dent. Mat. 22:353-358).

Upon polymerization, shrinkage stresses transferred to the tooth can cause deformation of the cusp or enamel microcracks (Davidson and Feilzer, 1997, J. Dent. Res. 25:435-440; Suliman et al., 1993, J. Dent. Res. 72(11):1532-1536; Suliman et al., 1993, J. Dent. Res. 9(1):6-10), and stress at the tooth-composite interface may cause adhesive failure, initiation of microleakage and recurrent caries. In addition, significant increases in volumetric shrinkage and shrinkage stress are experienced when the double bond conversion is increased to reduce the leachable monomer (Lu et al., 2004, J. Biomed. Mat. Res. Part B—Applied Biomat. 71B:206-213). This trade-off of conversion and shrinkage has been an inherent problem with composite restorative materials since their inception.

Recently, thiol-enes have been investigated as alternatives to dimethacrylate dental restorative materials (Lu et al., 2005, Dent. Mat., 21(12):1129-1136). The reactions proceed via a step growth addition mechanism that comprises the addition of a thiyl radical through a vinyl functional group and subsequent chain transfer to a thiol, regenerating the thiyl radical (Jacobine, A. F. Radiation Curing in Polymer Science and Technology III, Polymerisation Mechanisms; Fouassier, J. D.; Rabek, J. F., Ed.; Elsevier Applied Science, London, 1993; Chapter 7, 219; Hoyle et al., 2004, J. Pol. Sci.: Part A: Pol. Chem. 42:5301-5338; Cramer and Bowman, 2001, J. Pol. Sci. Part A. Pol. Chem. 39(19):3311; Cramer et al., 2003, Macromol. 36(12):4631; Cramer et al., 2003, Macromol. 36(21):7964; Reddy et al., 2006, Macromol. 39(10):3673). The step-growth polymerization mechanism results in shorter polymer chains and delayed gelation, resulting in reduced volume shrinkage and shrinkage stress. It is well known that in thiol-ene step growth polymerizations, the thiol and ene components must be present in a 1:1 stoichiometric ratio of functional groups to achieve complete conversion and maximize polymer mechanical properties (Morgan et al., 1977, J.

Polym. Sci. A, Polym. Chem. 627; Jacobine et al., 1992, J. Appl. Pol. Sci. 45(3):471-485; Cramer and Bowman, 2001, J. Pol. Sci. Part A. Pol. Chem. 39(19):3311; Hoyle et al., 2004, J. Pol. Sci.: Part A: Pol. Chem. 42:5301-5338). The high functional group conversion of thiol-ene polymers significantly mitigates the problems associated with current dimethacrylate resin systems which are associated with incomplete double bond conversion. Besides the impact of the polymerization mechanism on the gel point conversion and network formation, the thiol-ene systems have advantageous curing kinetics demonstrating rapid polymerization rates, high overall functional group conversion, and little sensitivity to oxygen inhibition (Lu et al., 2005, Dent. Mat. 21(12):1129-1136; Cramer et al., 2002, Macromol. 35:5361; Hoyle et al., 2004, J. Pol. Sci.: Part A: Pol. Chem. 42:5301-5338).

Most importantly for dental restorative materials, thiol-enes exhibit reduced shrinkage and shrinkage stress due to the step growth mechanism and delayed gel point conversion (Chiou et al., 1997, Macromol. 30:7322; Lu et al., 2005, Dent. Mat., 21(12):1129-1136). As a result of the delayed gel point, much of the shrinkage occurs before gelation, which dramatically reduces the shrinkage stress in the final polymer material.

The thiol-ene polymerization has also demonstrated thicker curing depth than methacrylate based resin systems. This can reduce the patient's chair-time since one-step curing is feasible, especially for large cavity filling, where incremental filling has to be applied using current dental composite systems. In addition, the thick cure depth and lack of oxygen inhibition of thiol-ene systems leads to fewer filling and curing steps during restorations, compared with the incremental filling technique using current dimethacrylate dental resin systems.

Unfortunately, despite several advantages of the thiol-ene resin systems for use as dental restorative materials, previous studies have also shown that traditional binary thiol-ene systems exhibit mechanical properties that are not ideal; specifically low flexural modulus and strength relative to dimethacrylate resins (Lu et al., 2005, Dent. Mat., 21(12):1129-1136).

Previous experiments utilizing methacrylate-thiol and acrylate-thiol systems have shown that methacrylate and acrylate functional groups are preferentially consumed due to their participation in both step and chain growth addition reactions (Cramer and Bowman, 2001, J. Pol. Sci. Part A. Pol. Chem. 39(19):3311; Lee et al., Macromol. 40(5), 1466, 2007; Lecamp et al., Polymer 2001, 42, 2727). However, to date, only 1:1 thiol-ene stoichiometry has been investigated in acrylate-thiol-ene and methacrylate-thiol-ene systems (Senyurt et al., 2007, Macromol. 40(14):4901-4909; Wei et al., 2007, J. Pol. Sci. Part A-Pol. Chem. 45(5):822-829; Lee et al., 2007, Macromol. 40(5):1466). Low ene conversion has been reported in these systems in the cases where both (meth) acrylate and ene functional group conversions have been resolved in FTIR (Lee et al., 2007, Macromol. 40(5):1466; Cramer et al., 2010, Dent. Mater. 26(1):21-28).

There is thus a need in the art for novel rapidly curing dental restorative materials with improved monomer conversion and mechanical properties. Such materials should present reduced volumetric shrinkage and shrinkage stress. The present invention fulfills these needs.

BRIEF SUMMARY OF THE INVENTION

The invention includes a photopolymerizable dental restorative composition comprising polymerizable monomers. In one preferred embodiment, about 50% to about 70% of the total weight of the polymerizable monomers is a methacrylate monomer, the balance by weight of the polymerizable monomers is a mixture of a thiol monomer and an ene monomer; and, the molar ratio of thiol functional groups from the thiol monomer relative to the ene functional groups from the ene monomer is greater than about 1:1.

In one embodiment, the molar ratio of the thiol functional groups to the ene functional groups is equal to or greater than about 1.5:1. In another embodiment, the molar ratio of the thiol functional groups to the ene functional groups is equal to or greater than about 1.75:1. In yet another embodiment, the molar ratio of the thiol functional groups to the ene functional groups is equal to or greater than about 2:1. In yet another embodiment, the composition further comprises a photoinitiator. In yet another embodiment, the photoinitiator comprises a visible light activated photoinitiator, a UV light activated photoinitiator, or a combination thereof. In yet another embodiment, the photoinitiator is selected from the group consisting of (2,4,6-trimethyl benzoyl)phosphine oxide, camphorquinone, bis(eta 5-2,4-cyclopentadien-1-yl)bis[2,6-difluoro-3-(1H-pyrrol-1-yl)phenyl]titanium, 1-hydroxy-cyclohexyl-phenylketone, 2,2-dimethoxy-2-phenylacetophenone, and any combinations thereof. In yet another embodiment, the composition further comprises a polymerization accelerator. In yet another embodiment, the composition further comprises a polymerization inhibitor. In yet another embodiment, the composition further comprises a filler in an amount of up to 90% by weight with respect to the total weight of the filled composition. In yet another embodiment, the filler is about 60 to about 85% by weight with respect to the total weight of the filled composition. In yet another embodiment, the composition comprises about 50% to about 70% by weight of the methacrylate monomer; and about 30% to about 50% by weight of the combined weight of the thiol monomer and the ene monomer. In yet another embodiment, the composition comprises about 50% to about 60% by weight of the methacrylate monomer; and about 40% to about 50% by weight of the combined weight of the thiol monomer and the ene monomer. In yet another embodiment, the composition comprises about 60% to about 70% by weight of the methacrylate monomer; and about 30% to about 40% by weight of the combined weight of the thiol monomer and the ene monomer. In yet another embodiment, the methacrylate monomer is a dimethacrylate monomer. In yet another embodiment, the methacrylate monomer is selected from the group consisting of ethylene glycol di(meth)acrylate, ethoxylated bisphenol-A dimethacrylate (EBPADMA), tetraethyleneglycol di(meth)acrylate (TEGDMA), poly(ethylene glycol)dimethacrylates, the condensation product of bisphenol A and glycidyl methacrylate, 2,2'-bis-[4-(3-methacryloxy-2-hydroxy propoxy)-phenyl]propane (BisGMA), hexanediol di(meth)acrylate, tripropylene glycol di(meth) acrylate, butanediol di(meth)acrylate, neopentyl glycol di(meth)acrylate, diethylene glycol di(meth)acrylate, triethylene glycol di(meth)acrylate, dipropylene glycol di(meth) acrylate, allyl(meth)acrylate, and any combinations thereof. In yet another embodiment, the methacrylate monomer is ethoxylated bisphenol-A dimethacrylate (EBPADMA). In yet another embodiment, the thiol monomer is selected from the group consisting of pentaerythritol tetra(3-mercaptopropionate) (PETMP), 1-octanethiol, butyl 3-mercaptopropionate, 2,4,6-trioxo-1,3,5-triazina-triy (triethyl-tris(3-mercapto propionate), 1,6-hexanedithiol, 2,5-dimercaptomethyl-1,4-dithiane, pentaerythritol tetramercaptoacetate, trimethylolpropane trimercaptoacetate, 2,3-dimercapto-1-propanol, 2-mercaptoethylsulfide, 2,3-(dimercaptoethylthio)-1-mercaptopropane, 1,2,3-trimercaptopropane, toluenedithiol, xylylenedithiol, 1,8-octanedithiol, 1-hexanethiol and trimethylolpropane tris(3-mercaptopropionate), glycol dimercaptopropionate, and any combinations thereof. In yet another embodiment, the thiol monomer is pentaerythritol tetra(3-mercaptopropionate) (PETMP). In yet another embodiment, the ene monomer comprises two or more ene functional groups. In yet another embodiment, the ene monomer is selected from the group consisting of triallyl-1,3,5-triazine-2,4,6-trione (TATATO), triethyleneglycol divinyl ether (TEGDVE), trimethylolpropane diallyl ether, dodecyl vinyl ether (DDVE), 1,6-heptadiyne, 1,7-octadiyne, bis-2,2-[4-(2-[norborn-2-ene-5-carboxylate]ethoxy)phenyl]propane (BPAEDN), 1,6-hexanediol di-(endo,exo-norborn-2-ene-5-carboxylate) (HDDN), trimethylolpropane tri-(norborn-2-ene-5-carboxylate) (TMPTN), pentaerythritoltri-(norborn-2-ene-5-carboxylate) (PTN3), pentaerythritol tetra-(norborn-2-ene-5-carboxylate) (PTN4), tricyclodecane dimethanol di-(endo, exo-norborn-2-ene-5-carboxylate) (TCDMDN), di(trimethylolpropane)tetra-(norborn-2-ene-5-carboxylate) (DTMPTN), and any combinations thereof. In yet another embodiment, the ene monomer is selected from the group consisting of triallyl-1,3,5-triazine-2,4,6-trione (TATATO), trimethylolpropane tri-(norborn-2-ene-5-carboxylate) (TMPTN), and any combinations thereof.

The invention also includes a method of preparing a shaped dental prosthetic device for use in a human mouth. The method comprises dispensing a photopolymerizable composition comprising polymerizable monomers, wherein: about 50% to about 70% of the total weight of the polymerizable monomers is a methacrylate monomer, and the balance by weight of the polymerizable monomers is a mixture of a thiol monomer and an ene monomer; a photoinitiator; and a filler. The composition may be dispensed using the available technologies known to those skilled in the art. The method further comprises shaping the composition into a form of the shaped dental prosthetic device. The composition may be shaped using the available technologies known to those skilled in the art. The method further comprises photopolymerizing the shaped composition. In one embodiment, the molar ratio of the thiol functional groups to the ene functional groups is equal to or greater than about 1.5:1.

The invention also includes a photopolymerizable dental restorative composition comprising polymerizable monomers, wherein about 50% to about 70% of the total weight of the polymerizable monomers is a methacrylate monomer, and the balance of the polymerizable monomers is a thiol monomer. In one embodiment, the composition further comprises a photoinitiator.

DETAILED DESCRIPTION OF THE INVENTION

Figure 1:
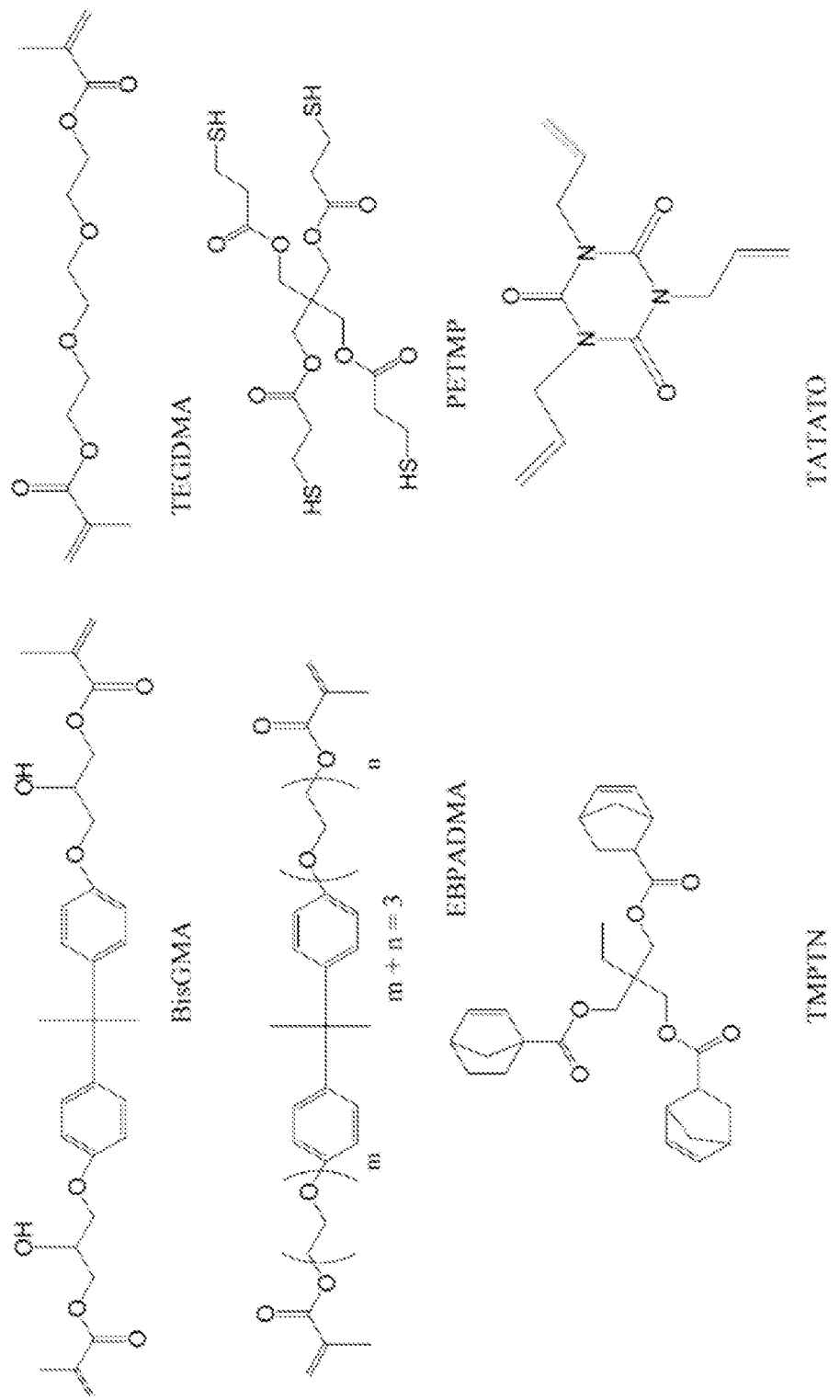
FIG. 1 illustrates various methacrylate, thiol and ene monomers.

The invention relates to a new photopolymerizable resin system for dental restorative materials. The resin system utilizes a thiol-ene component as the reactive diluent in dimethacrylate systems. The ternary resin system comprises a thiol monomer, an ene monomer and a dimethacrylate monomer. Although traditional thiol-ene systems utilize a 1:1 stoichiometric ratio of ene to thiol functional groups for optimum conversion, it is herein disclosed that use of an off-stoichiometric ratio of thiol:ene functional groups in favor of excess thiols results in enhanced overall functional group conversion, improved polymer mechanical properties, and reduced shrinkage stress of the ternary system when compared to either traditional dimethacrylate or thiol-ene resin systems.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in organic chemistry, and polymer chemistry are those well known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

The term "aliphatic" or "aliphatic group" as used herein means a straight-chain or branched hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl" and "alkoxy," used alone or as part of a larger moiety include both straight and branched carbon chains. The terms "alkenyl" and "alkynyl" used alone or as part of a larger moiety shall include both straight and branched carbon chains.

The terms "haloalkyl," "haloalkenyl" and "haloalkoxy" means alkyl, alkenyl or alkoxy, as the case may be, substituted with one or more halogen atoms. The term "halogen" or "halo" means F, Cl, Br or I.

The term "heteroatom" means nitrogen, oxygen, or sulfur and includes any oxidized form of nitrogen and sulfur, and the quaternized form of any basic nitrogen.

The terms "mercapto" or "thiol" refer to an —SH substituent, or are used to designate a compound having an —SH substituent.

The term "aryl" used alone or in combination with other terms, refers to monocyclic, bicyclic or tricyclic carbocyclic ring systems having a total of five to fourteen ring members, wherein at least one ring in the system is aromatic and wherein each ring in the system contains 3 to 8 ring members. The term "aryl" may be used interchangeably with the term "aryl ring".

The term "aralkyl" refers to an alkyl group substituted by an aryl. The term "aralkoxy" refers to an alkoxy group. The term "heterocycloalkyl," "heterocycle," "heterocyclyl" or "heterocyclic" as used herein means monocyclic, bicyclic or tricyclic ring systems having five to fourteen ring members in which one or more ring members is a heteroatom, wherein each ring in the system contains 3 to 7 ring members and is non-aromatic.

The term "monomer" refers to any discreet chemical compound of any molecular weight.

Thiol bearing monomers suitable for embodiments of the present invention include any monomer having thiol (mercaptan or "SH") functional groups. Thiols are any of various organic compounds having the general formula RSH which are analogous to alcohols but in which sulfur replaces the oxygen of the hydroxyl group. Suitable thiol monomers have one or preferably more functional thiol groups and may be of any molecular weight. In one embodiment, the thiol monomer may be selected from one or more of aliphatic thiols, thiol glycolate esters, thiol propionate esters. Examples of suitable thiol bearing monomers include: pentaerythritol tetra(3-mercaptopropionate) (PETMP); 1-Octanethiol; Butyl 3-mercaptopropionate; 2,4,6-trioxo-1,3,5-triazina-triy (triethyl-tris(3-mercapto propionate); 1,6-Hexanedithiol; 2,5-dimercaptomethyl-1,4-dithiane; pentaerythritol tetramercaptoacetate, trimethylolpropane trimercaptoacetate, 2,3-dimercapto-1-propanol, 2-mercaptoethylsulfide, 2,3-(dimercaptoethylthio)-1-mercaptopropane, 1,2,3-trimercaptopropane, toluenedithiol, xylylenedithiol, 1,8-octanedithiol, 1-hexanethiol (Sigma-Aldrich, Milwaukee, Wis.); and trimethylolpropane tris(3-mercaptopropionate), and glycol dimercaptopropionate (Evans Chemetics LP, Iselin, N.J.).

Monomers having "-ene" or vinyl functional groups suitable for embodiments of the present invention include any monomer having one, or preferably more functional vinyl groups, i.e., reacting "C=C" or "C≡C" groups. The ene monomer can be selected from one or more compounds having vinyl functional groups. Vinyl functional groups can be selected from, for example, vinyl ether, vinyl ester, allyl ether, norbornene, diene, propenyl, alkene, alkyne, N-vinyl amide, unsaturated ester, N-substituted maleimides, and styrene moieties. Examples of suitable ene monomers include Triallyl-1,3,5-triazine-2,4,6-trione (TATATO); Triethyleneglycol divinyl ether (TEGDVE); Trimethylolpropane diallyl ether; 1,6-heptadiyne; 1,7-octadiyne; and Dodecyl vinyl ether (DDVE) and norbornene monomers. In one specific embodiment, the ene monomer is selected from Triallyl-1,3,5-triazine-2,4,6-trione (TATATO), 1-Octanethiol 1,6-hexanedithiol triethyleneglycol divinyl ether (TEGDVE), and Dodecyl vinyl ether (DDVE). In one preferred embodiment, the ene monomer is triallyl-1,3,5-triazine-2,4,6-(1H,3H,5H)-trione (TATATO).

In one embodiment, the ene monomer is a norbornene monomer. A "norbornene monomer" refers to any compound having a discrete chemical formula and having two or more norbornene pendent groups, or a reactive oligomer, or reactive polymer, or pre-polymer, having at least one, but preferably two or more norbornene groups. Suitable norbornene monomers include bis-2,2-[4-(2-[norborn-2-ene-5-carboxylate]ethoxy)phenyl]propane (BPAEDN), 1,6-hexanediol di-(endo,exo-norborn-2-ene-5-carboxylate) (HDDN), 2-((bicyclo[2.2.1]hept-5-enecarbonyloxy)methyl)-2-ethylpropane-1,3-diyl bis(bicyclo[2.2.1]hept-5-ene-2-carboxylate) (trimethylolpropane tri-(norborn-2-ene-5-carboxylate); TMPTN), pentaerythritoltri-(norborn-2-ene-5-carboxylate) (PTN3), pentaerythritol tetra-(norborn-2-ene-5-carboxylate) (PTN4), tricyclodecane dimethanol di-(endo, exo-norborn-2-ene-5-carboxylate) (TCDMDN), and di(trimethylolpropane) tetra-(norborn-2-ene-5-carboxylate) (DTMPTN). These norbornenes may be synthesized, for example, by the methods in Carioscia et al., 2007, J. Pol. Sci.: Part A: Pol. Chem. 45:5686-5696, which is incorporated herein by reference. Certain other norbornene monomers may be prepared by the methods of Jacobine et al., 1992, J. Appl. Pol. Sci. 45(3):471-485, which is incorporated herein by reference. In one preferred embodiment, the ene monomer is the norbornene monomer trimethylolpropane tri-(norborn-2-ene-5-carboxylate) (TMPTN).

The term "methacrylate monomer" refers to a discrete chemical compound which is an ester of methacrylic acid. Methacrylate monomers suitable for embodiments of the present invention include any monomer having one or preferably two or more methacrylate moieties. In one embodiment, the methacrylate monomer is a dimethacrylate monomer. As used herein, a "dimethacrylate monomer" is a monomer having two methacrylate moieties per molecule. The methacrylate monomer is selected from one or more dimethacrylate monomers. Unless otherwise specified or implied, the term "(meth)acrylate" or "methacrylate" includes both the methacrylate and the analogous acrylate. Examples of suitable dimethacrylate monomers include alkyldiol dimethacrylates: ethylene glycoldi(meth)acrylate, ethoxylated bisphenol-A dimethacrylate (EBPADMA), tetraethyleneglycol di(meth)acrylate (TEGDMA), poly(ethylene glycol)dimethacrylates, the condensation product of bisphenol A and glycidyl methacrylate, 2,2'-bis[4-(3-methacryloxy-2-hydroxy propoxy)-phenyl]propane (BisGMA), hexanediol di(meth)acrylate, tripropylene glycol di(meth)acrylate, butanediol di(meth)acrylate, neopentyl glycol di(meth)acrylate, diethylene glycol di(meth)acrylate, triethylene glycol di(meth)acrylate, dipropylene glycol di(meth)acrylate, allyl (meth)acrylate and derivatives thereof. In one preferred embodiment, the methacrylate monomer is selected from 2,2-bis[4-(2-hydroxy-3-methacryloyloxypropoxy)phenyl]propane (BisGMA), ethoxylated bisphenol-A dimethacrylate (EBPADMA), and triethylene glycol dimethacrylate (TEGDMA).

Compositions

The invention includes a photopolymerizable dental restorative composition comprising polymerizable monomers. In one preferred embodiment, about 50% to about 70% of the total weight of the polymerizable monomers is a methacrylate monomer, the balance by weight of the polymerizable monomers is a mixture of a thiol monomer and an ene monomer; and, the molar ratio of thiol functional groups from the thiol monomer relative to the ene functional groups from the ene monomer is greater than about 1:1.

In one embodiment, the molar ratio of the thiol functional groups to the ene functional groups is equal to or greater than about 1.5:1. In another embodiment, the molar ratio of the thiol functional groups to the ene functional groups is equal to or greater than about 1.75:1. In yet another embodiment, the molar ratio of the thiol functional groups to the ene functional groups is equal to or greater than about 2:1. In yet another embodiment, the composition further comprises a photoinitiator. In yet another embodiment, the photoinitiator comprises a visible light activated photoinitiator, a UV light activated photoinitiator, or a combination thereof. In yet another embodiment, the photoinitiator is selected from the group consisting of (2,4,6-trimethyl benzoyl)phosphine oxide, camphorquinone, bis(eta 5-2,4-cyclopentadien-1-yl)bis[2,6-difluoro-3-(1H-pyrrol-1-yl)phenyl]titanium, 1-hydroxy-cyclohexyl-phenylketone, 2,2-dimethoxy-2-phenylacetophenone, and any combinations thereof. In yet another embodiment, the composition further comprises a polymerization accelerator. In yet another embodiment, the composition further comprises a polymerization inhibitor. In yet another embodiment, the composition further comprises a filler in an amount of up to 90% by weight with respect to the total weight of the filled composition. In yet another embodiment, the filler is about 60 to about 85% by weight with respect to the total weight of the filled composition. In yet another embodiment, the composition comprises about 50% to about 70% by weight of the methacrylate monomer; and about 30% to about 50% by weight of the combined weight of the thiol monomer and the ene monomer. In yet another embodiment, the composition comprises about 50% to about 60% by weight of the methacrylate monomer; and about 40% to about 50% by weight of the combined weight of the thiol monomer and the ene monomer. In yet another embodiment, the composition comprises about 60% to about 70% by weight of the methacrylate monomer; and about 30% to about 40% by weight of the combined weight of the thiol monomer and the ene monomer. In yet another embodiment, the methacrylate monomer is a dimethacrylate monomer. In yet another embodiment, the methacrylate monomer is selected from the group consisting of ethylene glycol di(meth)acrylate, ethoxylated bisphenol-A dimethacrylate (EBPADMA), tetraethyleneglycol di(meth)acrylate (TEGDMA), poly(ethylene glycol)dimethacrylates, the condensation product of bisphenol A and glycidyl methacrylate, 2,2'-bis-[4-(3-methacryloxy-2-hydroxy propoxy)-phenyl]propane (BisGMA), hexanediol di(meth)acrylate, tripropylene glycol di(meth) acrylate, butanediol di(meth)acrylate, neopentyl glycol di(meth)acrylate, diethylene glycol di(meth)acrylate, triethylene glycol di(meth)acrylate, dipropylene glycol di(meth) acrylate, allyl(meth)acrylate, and any combinations thereof. In yet another embodiment, the methacrylate monomer is ethoxylated bisphenol-A dimethacrylate (EBPADMA). In yet another embodiment, the thiol monomer is selected from the group consisting of pentaerythritol tetra(3-mercaptopropionate) (PETMP), 1-octanethiol, butyl 3-mercaptopropionate, 2,4,6-trioxo-1,3,5-triazina-triy (triethyl-tris(3-mercapto propionate), 1,6-hexanedithiol, 2,5-dimercaptomethyl-1,4-dithiane, pentaerythritol tetramercaptoacetate, trimethylolpropane trimercaptoacetate, 2,3-dimercapto-1-propanol, 2-mercaptoethylsulfide, 2,3-(dimercaptoethylthio)-1-mercaptopropane, 1,2,3-trimercaptopropane, toluenedithiol, xylylenedithiol, 1,8-octanedithiol, 1-hexanethiol and trimethylolpropane tris(3-mercaptopropionate), glycol dimercaptopropionate, and any combinations thereof. In yet another embodiment, the thiol monomer is pentaerythritol tetra(3-mercaptopropionate) (PETMP). In yet another embodiment, the ene monomer comprises two or more ene functional groups. In yet another embodiment, the ene monomer is selected from the group consisting of triallyl-1,3,5-triazine-2,4,6-trione (TATATO), triethyleneglycol divinyl ether (TEGDVE), trimethylolpropane diallyl ether, dodecyl vinyl ether (DDVE), 1,6-heptadiyne, 1,7-octadiyne, bis-2,2-[4-(2-[norborn-2-ene-5-carboxylate]ethoxy)phenyl]propane (BPAEDN), 1,6-hexanediol di-(endo,exo-norborn-2-ene-5-carboxylate) (HDDN), trimethylolpropane tri-(norborn-2-ene-5-carboxylate) (TMPTN), pentaerythritoltri-(norborn-2-ene-5-carboxylate) (PTN3), pentaerythritol tetra-(norborn-2-ene-5-carboxylate) (PTN4), tricyclodecane dimethanol di-(endo, exo-norborn-2-ene-5-carboxylate) (TCDMDN), di(trimethylolpropane)tetra-(norborn-2-ene-5-carboxylate) (DTMPTN), and any combinations thereof. In yet another embodiment, the ene monomer is selected from the group consisting of triallyl-1,3,5-triazine-2,4,6-trione (TATATO), trimethylolpropane tri-(norborn-2-ene-5-carboxylate) (TMPTN), and any combinations thereof.

The invention also includes a photopolymerizable dental restorative composition comprising polymerizable monomers, wherein about 50% to about 70% of the total weight of the polymerizable monomers is a methacrylate monomer, and the balance of the polymerizable monomers is a thiol monomer.

In one embodiment, the composition further comprises a photoinitiator.

As demonstrated herein, a 1:1 thiol-ene ratio is not optimum in ternary (meth)acrylate-thiol-ene systems. The thiol functional groups can react with both ene and methacrylate functional groups. However, the ene functional groups typically only react with thiol functional groups. Therefore, when a 1:1 ratio is utilized the thiol functional groups become a limiting reagent resulting in the ene functional groups achieving a relatively low overall conversion.

The flexural strength of the resin systems should be equivalent to, or higher, than the methacrylate controls to ensure that the materials are strong enough to function as a tooth. However, the highest flexural modulus value is not necessarily desired. A material with a very high modulus would be brittle and could shatter upon high impact without absorbing any of the pressure. A material with a very low modulus would be too soft and lack the toughness to act as a tooth. The results of the flexural testing show that the methacrylate-thiol-ene systems are able to function as a tooth with a good flexural modulus and increased flexural strength over the controls.

The ternary methacrylate-thiol-ene systems exhibit an increased conversion and depth of cure over the methacrylate controls, while still experiencing less volumetric shrinkage and shrinkage stress, along with decreased water solubility and sorption. The increased conversions not only strengthen important mechanical and wear resistance properties, but the biocompatibility of the systems will be improved for the ternary systems. The decrease in volume shrinkage and shrinkage stress will increase the longevity of the material for dental restorations.

As the ratio of thiol-to-ene in the ternary systems is increased, the materials maintain equivalent mechanical properties while experiencing improvements in other properties. The increased depth of cure and reduction in shrinkage stress may not be statistically significant, but conversion and volumetric shrinkage are improved with increases in thiol content. The increase in both methacrylate and allyl ether conversion can be attributed to the fact the thiol functional groups can react with both methacrylates and allyl ethers, but the allyl ether functional groups can react only with the thiol. Therefore if the amount of thiol and allyl ether in a system is stoichiometric, the thiols are consumed by methacrylates and allyl ethers and become the limiting reagent in the thiol-ene reaction. This results in a low allyl ether functional group conversion. As the ratio of thiol-to-ene is increased from 1:1 to 3:1, the allyl ether conversion is more than doubled along with a 7% increase in the methacrylate conversion.

As the thiol-to-ene ratio is increased to 3:1, there is also a nearly 20% decrease in the volumetric shrinkage of the ternary system. Volume shrinkage is proportional to double bond conversion only and is not dependent on thiol group conversion; therefore as the thiol concentration is increased there are fewer double bond groups available for volume shrinkage (Lu et al., 2005, J. Dent. Res. 84:822-826).

The improved mechanical properties, depth of cure, and water sorption and solubility with reduced volume shrinkage and shrinkage stress make ternary methacrylate/thiol-ene systems superior to systems based on a bulk dimethacrylate resin. The significant increase in functional group conversion and the decrease in volumetric shrinkage exhibited by methacrylatethiol-ene ternary systems with an off-stoichiometric ratio of thiol-to-ene results in a system that compensates for shortcomings of methacrylate-based composites and makes methacrylate-thiolene systems attractive as dental restorative materials.

The invention includes ternary (meth)acrylate-thiol-ene polymer resin systems where increasing the ratio of thiol to ene functional group stoichiometry results in an increase in the overall functional group conversion. Additionally, by incorporating more thiol content into the reaction, additional chain transfer in the step growth propagation is prevalent and results in further delayed gelation and reduced shrinkage stress.

The methacrylate-thiol-ene system exhibits a polymerization mechanism that is a combination of both step and chain growth polymerizations (Reddy et al., 2006, Macromol. 39(10):3681; Lee et al., 2007, Macromol. 40(5):1466). Due to the unique combination of both step and chain growth polymerizations, the optimum thiol:ene ratio deviates from the traditional 1:1 stoichiometry. Increasing the thiol:ene stoichiometry results in systems with equivalent flexural modulus, 6-20% reduced flexural strength, 5-33% reduced shrinkage stress, and up to 70% reduced shrinkage stress relative to traditional methacrylate resin systems such as ethoxylated bisphenol-A dimethacrylate/triethylene glycol dimethacrylate (EBPADMA/TEGDMA).

Employing thiol-enes as reactive diluents results in systems that exhibit the advantageous properties of both methacrylate and thiol-ene systems. Due to the strong homopolymerization tendency of methacrylate functional groups, the early stages of the reaction are dominated by methacrylate homopolymerization, resulting in further decreased shrinkage stress due to the thiol-ene component acting as a diluent (Lee et al., 2007, Macromol. 40(5):1473-1479).

Additionally, use of the thiol-ene as the reactive diluent replaces TEGDMA, which is prone to leaching as well as typically providing relatively high hydrophilicity. The methacrylatethiol-ene resin systems exhibit equivalent mechanical properties for flexural modulus and flexural strength, equivalent curing rates, increased overall functional group conversion, and reduced shrinkage stress relative to the dimethacrylate control systems.

The methacrylate-thiol-ene resin systems of the disclosure exhibit equivalent mechanical properties for flexural modulus and flexural strength, equivalent curing rates, increased overall functional group conversion, and reduced shrinkage stress relative to the dimethacrylate control systems.

The invention includes a methacrylate-thiol-ene polymer resin system which comprises a methacrylate monomer, a thiol monomer and an ene monomer. In one embodiment, the methacrylate monomer is present in at least 50 wt % relative to the total weight of all polymerizable monomers. In another embodiment, the combined weight of the thiol monomer and the ene monomer is at least 10 wt % relative to the weight of all polymerizable monomers. In another embodiment, the resin system comprises 50 to 80% by weight of the methacrylate monomer and 20 to 50% by weight of the combined weight of the thiol and ene monomers; preferably 60 to 70% by weight of the methacrylate monomer and 30 to 40% by weight of the combined weight of the thiol and ene monomers, relative to the total weight of all polymerizable monomers. In the methacrylate-thiol-ene polymer resin systems, the molar ratio of thiol functional groups from the thiol monomer relative to the ene functional groups from the ene monomer is greater than about 1:1; preferably greater than about 2:1.

In one embodiment, the methacrylate monomer is a dimethacrylate monomer. In a specific embodiment, the methacrylate monomer is EBPADMA. In another embodiment, the thiol monomer is a multithiol monomer. In a specific embodiment, the thiol monomer is PETMP which has four thiol functional groups per molecule as illustrated in FIG. 1. In a further embodiment, the ene monomer is a multiene monomer. In a specific embodiment, the ene monomer has three ene functional groups per molecule. In another specific embodiment, the ene monomer is selected from TMPTN or TATATO.

In specific embodiments, the methacrylate-thiol-ene polymer resin system is selected from the group consisting of EBPADMA/PETMP/TATATO and EBPADMA/PETMP/TMPTN. In one embodiment, the weight ratio of methacrylate monomer to the combined weight of the thol and ene monomer is selected from 70/30 or 60/40. In another specific embodiment, the molar ratio of thiol functional groups to ene functional groups is selected from 3:1, or 2:1.

Methacrylate-thiol-ene resin systems may also include and/or utilize various initiators, fillers, inhibitors and accelerators depending on the application.

In one embodiment, the free radical initiated photopolymerization may be photoinitiated by any light wavelength range within the ultraviolet (about 200 to about 400 nm) and/or visible light spectrum (about 380 to about 780 nm). The choice of the wavelength range can be determined by the photoinitiator employed. In one embodiment, a full spectrum light source, e.g. a quartz-halogen xenon bulb, may be utilized for photopolymerization. In another embodiment, a wavelength range of about 320 to about 500 nm is employed for photopolymerization.

In one embodiment, the resin further comprises a polymerization photoinitiator. In one embodiment, any radical photoinitiator may be employed. In another embodiment, a photoinitiator responsive to visible light is employed. In one embodiment, the photoinitiator is a bis acyl phosphine oxide (BAPO). In a specific embodiment, the BAPO photoinitiator is phenyl bis(2,4,6-trimethyl benzoyl)phosphine oxide (Irgacure 819, Ciba). In another embodiment, the photoinitiator is a metallocene initiator. In a specific embodiment, the metallocene initiator is Bis(eta 5-2,4-cyclopentadien-1-yl)Bis[2,6-difluoro-3-(1H-pyrrol-1-yl)phenyl]titanium (Irgacure 784, Ciba). In another embodiment, if photopolymerization using visible light is desired, camphorquinone (CQ) may be used as an initiator, in combination with an accelerator, such as, for example, ethyl 4-dimethylaminobenzoate (EDAB). Alternatively, if ultraviolet (UV) photopolymerization is desired, then an appropriate UV light activated photoinitiator may be employed. For example, the photoinitiator can be selected from an alpha-hydroxyketone, such as 1-hydroxy-cyclohexylphenylketone (Irgacure 184, Ciba); a benzyldimethyl-ketal, such as 2,2-dimethoxy-2-phenylacetophenone (DMPA, e.g. Irgacure 651, Ciba), or a number of other commercially available photoinitiators may be used as an initiator. Photoinitiators can be used in amounts ranging from about 0.01 to about 5 weight percent (wt %). In one specific embodiment, 0.25 wt % (2,4,6-trimethyl benzoyl)phosphine oxide (Irgacure 819) is used as the photoinitiator. In another specific embodiment, 0.3 wt % CQ is used as an initiator for visible light experiments, along with 0.8 wt % ethyl 4-(dimethylamino)benzoate (commonly known as EDMAB or EDAB). In another specific embodiment, 0.2 wt % DMPA is used as an initiator for UV polymerization.

In one embodiment, one or more accelerators are utilized in the photopolymerization. Amine accelerators may be used as polymerization accelerators, as well as other accelerators. Polymerization accelerators suitable for use are the various organic tertiary amines well known in the art. In visible light curable compositions, the tertiary amines are generally acrylate derivatives such as dimethylaminoethyl methacrylate and, particularly, diethylaminoethyl methacrylate (DEAEMA), EDAB and the like, in an amount of about 0.05 to about 0.5 wt %. The tertiary amines are generally aromatic tertiary amines, preferably tertiary aromatic amines such as EDAB, 2-[4-(dimethylamino)phenyl]ethanol, N,N-dimethyl-p-toluidine (commonly abbreviated DMPT), bis(hydroxyethyl)-p-toluidine, triethanolamine, and the like. Such accelerators are generally present at about 0.5 to about 4.0 wt % in the polymeric component. In one embodiment, 0.8 wt % EDAB is used in visible light polymerization.

In one embodiment, the resin compositions of the disclosure further comprise one or more fillers. In one embodiment, fillers are used to increase the viscosity of the dental restorative material, to tailor the hydrophilicity of the dental impression material, and to increase the stiffness (rubbery modulus) of the cured impression. The filled compositions can include one or more of the inorganic fillers currently used in dental restorative materials, the amount of such filler being determined by the specific function of the filled materials. Thus, for example, in one embodiment dental impression materials may be mixed with one or more inorganic filler compounds such as barium, ytterbium, strontium, zirconia silicate and/or amorphous silica to match the color and opacity to a particular use or tooth. The filler can be a silanized filler. The filler is typically in the form of particles with a size ranging from 0.01 to 5.0 micrometers. In one embodiment, the filler is a hydrophobic fumed silica. In one specific embodiment, the hydrophobic fumed silica filler is composed of nanoparticles or nanoclusters.

A nanoparticle is defined as any particle less than 100 nanometers (nm) in diameter. A nanocluster is an agglomeration of nanoparticles. In one embodiment, utilization of nanoclusters in a nanosized filler can be exploited to increase the load and improve some mechanical properties. Other suitable fillers are known in the art, and include those that are capable of being covalently bonded to the impression material itself or to a coupling agent that is covalently bonded to both. Examples of suitable filling materials include but are not limited to, barium glass, ytterbium nanoglasses and nanoclusters, fumed silica, silica, silicate glass, quartz, barium silicate, strontium silicate, barium borosilicate, strontium borosilicate, borosilicate, lithium silicate, lithium alumina silicate, amorphous silica, ammoniated or deammoniated calcium phosphate and alumina, zirconia, tin oxide, and titania. Some of the aforementioned inorganic filling materials and methods of preparation thereof are disclosed in U.S. Pat. No. 4,544,359 and U.S. Pat. No. 4,547,531; pertinent portions of each of which are incorporated herein by reference. In one embodiment, the filler is a mixture of barium glass, ytterbium nanoglasses and nanoclusters, and fumed silica. In one specific embodiment, the filler is 85 wt % 0.5 micron barium glass, 10 wt % ytterbium 40 nm nanoglass and nanoclusters, 2.5 wt % Aerosil fumed silica, and 2.5 wt % Cabosil fumed silica. In another embodiment, the filler is a mixture of 90% 0.4 µm Schott glass and 10 wt % Aerosol OX-50. The above described filler materials may be combined with the resins of the disclosure to form a dental composite material with high strength along with other beneficial physical and chemical properties.

In one embodiment, suitable fillers are those having a particle size in the range from about 0.01 to about 5.0 micrometers, mixed with a silicate colloid of about 0.001 to about 0.07 micrometers. The filler may be utilized in the filled resin compositions of the disclosure in the amount of from about 40 wt % to about 90 wt %; preferably about 60 wt % to 85 wt %; more preferably about 70 wt % to about 80 wt % of the total weight of the composition. In one specific embodiment, 72.5 wt % filler is utilized in the filled resin composition. In another specific embodiment, 60 wt % filler is utilized in the filled resin composition.

In another embodiment, the resin composition further comprises a polymerization inhibitor, or stabilizer. Examples of inhibitors include hydroquinone monomethyl ether (MEHQ), aluminum-N-nitrosophenylhydroxylamine, and 2,6-di-tertbutyl-4-methylphenol (BHT). In a specific embodiment, the inhibitor is aluminum-N-nitrosophenylhydroxylamine (Q1301, Wako Pure Chemical, Osaka, Japan). The optional inhibitor may be utilized in the amount of from about 0.001 wt % to about 0.5 wt %, or about 0.01 wt % to about 0.1 wt % of the resin composition. In one specific embodiment, the inhibitor aluminum-N-nitrosophenylhydroxylamine is utilized as 0.035 wt % of the resin. In another specific embodiment, aluminum-N-nitrosophenylhydroxylamine is utilized at 0.075 wt % of the total weight of the filled resin composition.

In one embodiment, the resin composition further comprises a UV absorber. The UV absorber can be selected from, for example, 5-benzoyl-4-hydroxy-2-methoxy-benzenesulfonic acid, Uvinul® 3000 from BASF Corp., and other various benzophenones, e.g. UV-5411 from American Cyanamid. The UV absorber can be present in from about 0.05 to about 5 wt %; preferably less than about 0.5 wt % of the weight of the total weight of the filled composition. In one specific embodiment, Uvinul® 3000 is present in 0.10 wt % of the total weight of the filled composition.

The invention includes a new resin system for use in dental restorative materials. The polymerizable resin system comprises a methacrylate monomer, a thiol monomer, and an ene monomer. In one embodiment, the methacrylate is present from about 40 wt % to about 90 wt %, preferably about 50 wt % to about 80 wt %, more preferably about 60 wt % to about 70 wt % of the total weight of the unfilled resin. In another embodiment, the combined weight of the thiol and ene components are from about 10 wt % to about 60 wt % of the unfilled resin, preferably about 20 wt % to about 50 wt %, more preferably about 30 wt % to about 40 wt % of the total weight of the unfilled resin. In one embodiment, the molar ratio of thiol to ene functional groups in the resin composition is greater than about 1:1; preferably greater than about 1.5:1; more preferably greater than about 1.75:1; more preferably greater than about 2:1.

In one embodiment, the resin composition further comprises a photoinitiator. In optional embodiments, the resin further comprises a filler. In another embodiment, the thiolenemethacrylate resin further comprises an inhibitor.

The invention includes a range of visible light cured methacrylate-thiol and methacrylate-thiol-ene systems. In one embodiment, as illustrated in Table 1, relative to the Bis-GMA/TEGDMA control resin, methacrylate-thiol-ene systems exhibit equivalent cure speed and up to 38% increased methacrylate functional group conversion for the EBPADMA/PETMP:TATATO system and up to 28% increased methacrylate functional group conversion for the EBPADMA/PETMP:TMPTN system. In another embodiment, as illustrated in Table 1, relative to the EBPADMA/TEGDMA control resin, methacrylate-thiol-ene systems exhibit equivalent cure speed and up to 27% increased methacrylate functional group conversion for the EBPADMA/PETMP: TATATO system and up to 17% increased methacrylate functional group conversion for the EBPADMA/PETMP:TMPTN system. In yet another embodiment, increasing the thiol-ene content or thiol to ene ratio increases the overall functional group conversions.

In one embodiment, the increased functional group conversion improves the biocompatibility of the methacrylate-thiol-ene systems as dental restorative materials. In a specific embodiment, the ternary systems exhibit decreased cytotoxicity when compared to dimethacrylate resin systems.

In one embodiment, in the methacrylate-thiol-ene systems, increasing the thiol to ene stoichiometric ratio in both the systems containing either ene TATATO or TMPTN reduces shrinkage stress without compromising flexural modulus. However, flexural strength is slightly reduced. In the methacrylate-thiol-ene systems, increasing the thiol-ene content from 30 to 40% resulted in further reductions in shrinkage stress. However, in the EBPADMA/PETMP:TATATO unfilled system there was also a significant drop in both flexural modulus and flexural strength. In the EBPADMA/PETMP:TMPTN unfilled system, increasing the thiol-ene content from 30 to 40% did not significantly impact flexural modulus or strength. Relative to the EBPADMA/TEGDMA control, the EBPADMA/PETMP:TATATO system exhibits up to 47% reduced shrinkage stress and is achieved without significant reductions in flexural modulus or strength. In the EBPADMA/PETMP:TMPTN system, up to 72% reduced shrinkage stress is achieved without significantly reducing flexural modulus or strength.

In another embodiment, the methacrylate-thiol-ene systems exhibit equivalent polymerization kinetics and increased overall functional group conversion, along with reduction in shrinkage stress while maintaining equivalent flexural modulus and near equivalent flexural strength relative to the control dimethacrylate resins. In this embodiment, the combination of equivalent flexural modulus and reduced shrinkage stress in methacrylate-thiol-ene systems results in composites with superior characteristics relative to composites comprising traditional dimethacrylate resin systems.

In one specific embodiment, the methacrylate-thiol-ene filled resin composite system contains Ethoxylated Bis-Phenol A Dimethacrylate (EBPADMA) 14.891 wt %; Pentaerythritol Tetra(3-mercaptopropionate) (PETMP) 7.428 wt %; Triallyl Triazine Trione (TATATO) 2.519 wt %; aluminum N-nitrosophenylhydroxylamine 0.010 wt %; Uvinul 3000 0.100 wt %; Irgacure 819 0.075 wt %; Schott Glass 8235 0.4 µm 9.4% Sil 59.982 wt %; Ytterbium Glass SG-YBF 40-4-3% Sil 11.247 wt %; and Aerosil OX 50 PA-Sil 3.749 wt %.

In another specific embodiment, the methacrylate-thiol-ene filled resin composite system contains ethoxylated Bis-Phenol A Dimethacrylate (EBPADMA) 14.895 wt %; pentaerythritol Tetra(3-mercaptopropionate) (PETMP) 5.923 wt %; trimethylolpropane trinorbornene 3.998 wt %; aluminum N-nitrosophenylhydroxylamine 0.010 wt %; Uvinul 3000 0.100 wt %; Irgacure 819 0.075 wt %; Schott Glass 8235 0.4 µm 9.4% Sil 59.999 wt %; Ytterbium Glass SG-YBF 40-4-3% Sil 11.250 wt %; and Aerosil OX 50 PA-Sil 3.750 wt %.

In a further embodiment, the invention includes methacrylate-thiol resin systems which exhibit reduced shrinkage stress relative to the dimethacrylate controls. The methacrylatethiol resin systems comprise one or more methacrylate monomers and one or more thiol monomers. In one embodiment, in the methacrylate-thiol systems the methacrylate is present in at least 50 wt % of the weight of all polymerizable monomers and the balance of polymerizable monomers are thiol monomers. In another embodiment, the thiol monomer is present in from about 1 wt % to about 50 wt %; preferably about 10 wt % to about 30 wt % of the total weight of polymerizable monomers in the methacrylate-thiol resin system.

Methods

The invention includes a method of preparing a shaped dental prosthetic device for use in a human mouth. The method comprises dispensing a photopolymerizable composition comprising polymerizable monomers, wherein: about 50% to about 70% of the total weight of the polymerizable monomers is a methacrylate monomer, and the balance by weight of the polymerizable monomers is a mixture of a thiol monomer and an ene monome; a photoinitiator; and a filler. The composition may be dispensed using the available technologies known to those skilled in the art. The method further comprises shaping the composition into a form of the shaped dental prosthetic device. The composition may be shaped using the available technologies known to those skilled in the art. The method further comprises photopolymerizing the shaped composition. In one embodiment, the molar ratio of the thiol functional groups to the ene functional groups is equal to or greater than about 1.5:1.

In one embodiment, the filled resin is utilized as a photocurable dental restorative material. The photocurable restorative materials can be sold in separate syringes or single-dose capsules of different shades. If provided in a syringe, the user dispenses (by pressing a plunger or turning a screw adapted plunger on the syringe) the necessary amount of restorative material from the syringe onto a suitable mixing surface. Then the material is placed directly into the cavity, mold, or location of use. If provided as a single-dose capsule, the capsule is placed into a dispensing device that can dispense the material directly into the cavity, mold, and such. After the restorative material is placed, it is photopolymerized or cured by exposing the restorative material to the appropriate light source. The resulting cured polymer may then be finished or polished as necessary with appropriate tools. Such dental restoratives can be used for direct anterior and posterior restorations, core build-ups, splinting and indirect restorations including inlays, onlays and veneers.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Experimental work on the methacrylate-thiol-ene polymer embodiments as dental restorative materials was performed to demonstrate the feasibility and advantages of these polymers over currently used dental restorative materials. Values in parenthesis in all Tables represent standard deviations.

Materials

Dicyclopentadiene, trimethylolpropane triacrylate, and phenothiazine (PTZ) were purchased from Aldrich and utilized for norbornene monomer synthesis. The monomer triallyl-1,3,5-triazine-2,4,6-(1H,3H,5H)-trione (TATATO) was also purchased from Aldrich. The photoinitiator Irgacure 819 was donated by Ciba Specialty Chemicals (Tarrytown, N.Y.). The inhibitor aluminum N-nitrosophenylhydroxylamine (Q1301) was donated by Wako Pure Chemicals (Osaka, Japan). The monomers 2,2-bis[4-(2-hydroxy-3-methacryloyloxypropoxy)phenyl]propane (BisGMA), ethoxylated bisphenol-A dimethacrylate (EBPADMA), and triethylene glycol dimethacrylate (TEGDMA) were donated by Esstech Inc. (Essington, Pa.). Pentaerythritol tetra(3-mercaptopropionate) (PETMP) was donated by Evans Chemetics (Waterloo, N.Y.). All chemicals were used as received. The norbornene monomer trimethylolpropane tri-(norborn-2-ene-5-carboxylate) (TMPTN) was synthesized by a procedure that is described elsewhere (Carioscia et al., 2007, J. Pol. Sci. Part A: Pol. Chem. 45(23): 5686-5696). Chemical structures of monomers are illustrated in FIG. 1. The inorganic glass filler is comprised of 0.4 µm glass, or 0.5 µm barium glass from Schott (Elmsford, N.Y.), ytterbium 40 nm nanoglass and nanoclusters, Aerosil OX-50, and Cabosil fumed silicas were donated by Septodont, Confi-Dental Division (Louisville, Colo.).

Methods

All analyses were conducted using 0.3 wt % Irgacure 819 as the photoinitiator and were irradiated with 29 mW/cm$^2$ of light with an EXFO Acticure (Mississauga, Ontario, Canada) with 400-500 nm filter. Irradiation intensity was measured at the sample surface level with an International Light, Inc. Model IL1400A radiometer (Newburyport, Mass.).

Flexural Modulus and Strength

Samples were prepared using teflon molds measuring 2 mm×2 mm×25 mm and were cured under identical conditions as in the FTIR analysis. Polymer flexural strength and modulus were calculated using a 3-point flexural test, carried out with a hydraulic universal test system (858 Mini Bioix, MTS Systems Corporation, Eden Prairie, Minn., USA) using a span width of 10 mm and a crosshead speed of 1 mm/min. For each system, at least five duplicates were evaluated.

Fourier Transform Infrared Spectroscopy (FTIR)

Kinetic analysis was conducted using a Nicolet 750 Magna FTIR spectrometer (Madison, Wis.) with a KBr beam splitter and an MCT/A detector. Series scans were recorded at a rate of approximately 2 scans per second until the reaction was complete, as indicated by the functional group absorption peak no longer decreasing. Experiments were conducted in the near infrared (7000-4000 cm$^{-1}$) with samples placed between glass slides with a 1.0 mm glass spacer. Methacrylate functional group conversion was monitored utilizing the methacrylate absorption peak at 6,164 cm$^{-1}$ and the allyl ether absorption peak at 6,132 cm$^{-1}$. Methacrylate and allyl ether peak absorbances are overlapped in the near infrared and a Gaussian fitting peak deconvolution method was utilized to determine individual functional group conversions. The near infrared configuration is preferred when evaluating dental resins due to the 1 mm sample thickness that is more relevant to a clinical curing thickness. Norbornene functional groups do not exhibit a strong enough absorption in the near infrared to determine functional group conversion. For each composition, experiments were performed in triplicate.

Shrinkage Stress

Experiments were performed with a tensometer (American Dental Association Health Foundation), which monitors stress development using cantilever beam deflection theory. A detailed description of the tensometer and measurement technique is found elsewhere (Lu et al., 2005, Dent. Mat. 21(12): 1129-1136). Simultaneous conversion measurements are facilitated using remote near infrared transmitted through the polymer sample via fiber optic cables. Samples are placed between 6 mm glass rods and measured 1.5 mm in thickness. Irradiation intensity is measured at the tip of the 6 mm glass rod. As this diameter is less than the diameter of the radiometer detector, the measured intensity of 29 mW/cm$^2$ is less than the actual irradiation intensity. For each composition, experiments were performed in triplicate.

Example 1

Polymerization Kinetics & Conversion

Polymerization kinetics were monitored for various methacrylate-thiol-ene, methacrylate-thiol and dimethacrylate control resins under identical curing conditions. All samples contained 0.3 wt % Irgacure 819, 0.035 wt % Q1301, and were irradiated at 29 mW/cm$^2$ with a 400-500 nm filter. Conversion of functional groups was monitored by FTIR.

Figure 2:
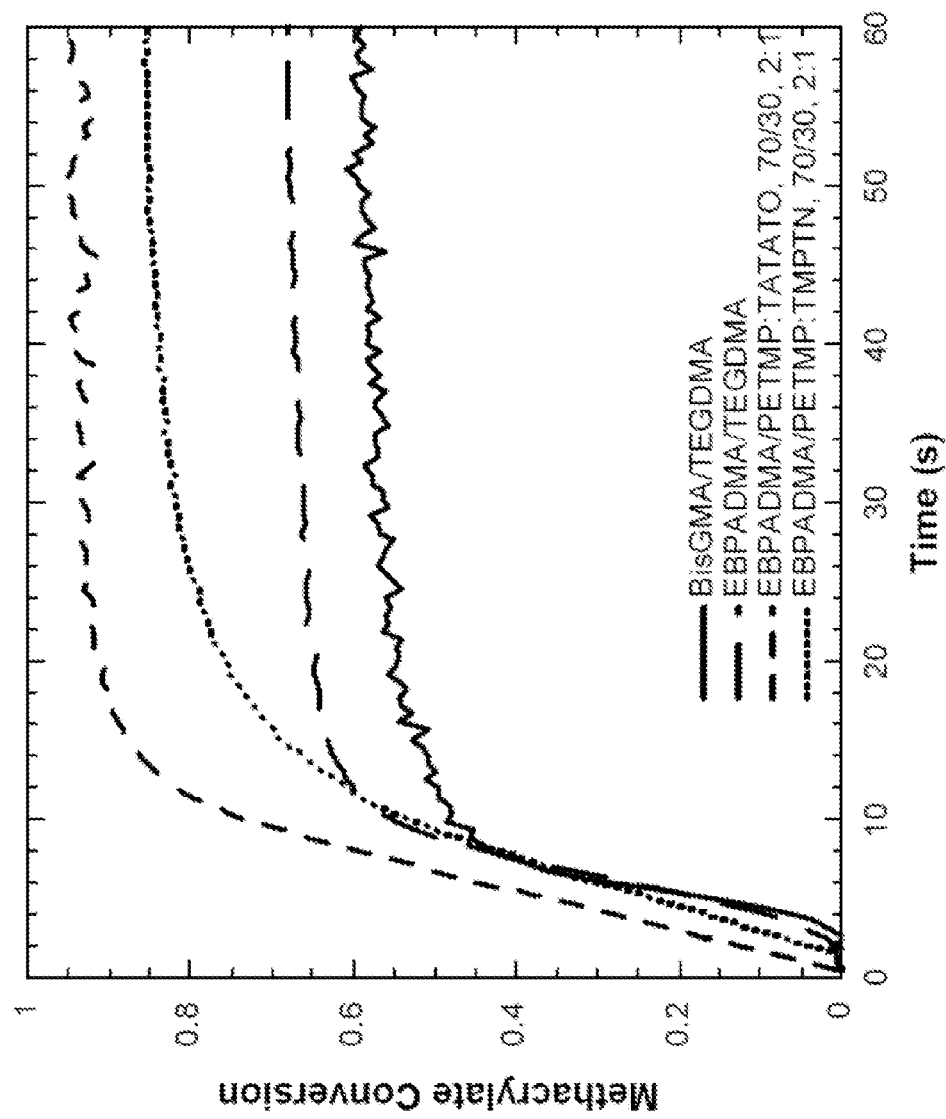
FIG. 2 illustrates methacrylate functional group conversion upon photopolymerization of two methacrylate control systems and two ternary methacrylate-thiol-ene resin systems.
Figure 3:
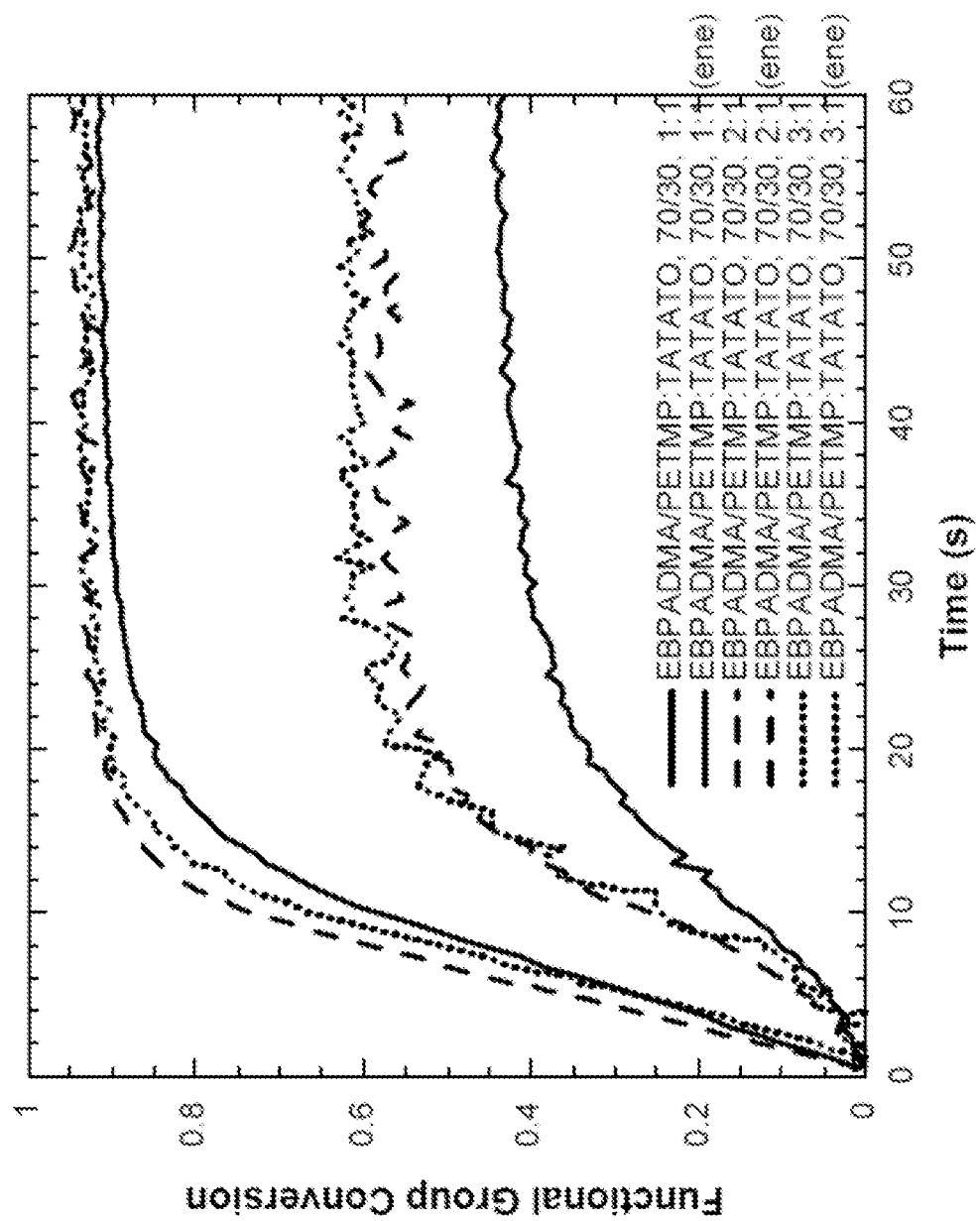
FIG. 3 illustrates both methacrylate and ene (ene) functional group conversion utilizing a methacrylate-thiol-ene system with EBPADMA/PETMP:TATATO, in a 70/30 weight percent of methacrylate (EBPADMA) to thiol:ene (PETMP:TATATO). The 1:1; 2:1 and 3:1 ratios represent the molar ratio of thiol (PETMP) to ene (TATATO) functional groups.
Figure 4:
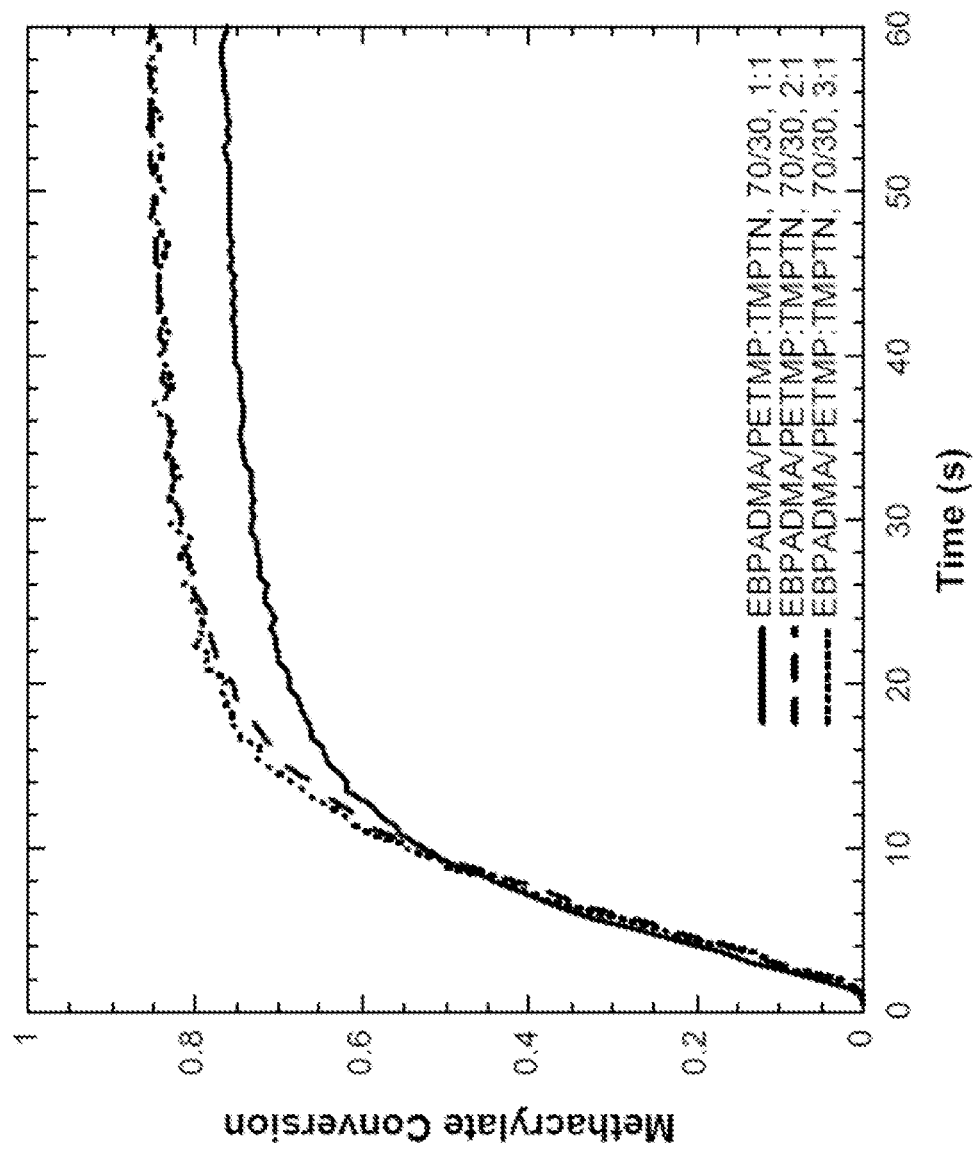
FIG. 4 illustrates methacrylate functional group conversion utilizing a methacrylatethiol-ene system with EBPADMA/PETMP:TMPTN, in a 70/30 weight percent of methacrylate (EBPADMA) to thiol:ene (PETMP:TMPTN). The 1:1; 2:1 and 3:1 ratios represent the molar ratio of thiol (PETMP) to ene (TMPTN) functional groups.

Functional group conversion data over time in various systems are illustrated in FIGS. 2-4. Final conversion for each system is shown in Table 1. FIG. 2 shows methacrylate conversion monitored over time for four resin systems. Two methacrylate control systems BisGMA/TEGDMA and EBPADMA/TEGMA, both at a 70/30 wt ratio, were compared to two methacrylate-thiol-ene systems: EBPADMA/PETMP:TATATO at 70 wt % methacrylate/30 wt % thiol-ene with a 2:1 stoichiometric ratio of thiol to ene functional groups and EBPADMA/PETMP:TMPTN at 70/30 wt ratio with a 2:1 stoichiometric ratio of thiol to ene functional groups. The methacrylate-thiol-ene systems exhibited more complete methacrylate conversion than the control methacrylate systems.

FIG. 3 shows both methacrylate and ene (ene) functional group conversion utilizing a methacrylate-thiol-ene system with EBPADMA/PETMP:TATATO, in a 70/30 weight percent of methacrylate (EBPADMA) to thiol:ene (PETMP:TATATO). The 1:1; 2:1 and 3:1 ratios represented the molar ratio of thiol (PETMP) to ene (TATATO) functional groups. The off-stoichiometric systems contained the same overall weight percent of thiol-ene resin, but the ratio of thiol to ene functional groups was 2:1, or 3:1 compared to the traditional 1:1 ratio of thiol to ene functional groups that was optimum for a step growth system. As the ratio of thiol to ene functional groups was increased in the EBPADMA/PETMP:TATATO 70/30 system, the ene functional group conversion increased from 45% for the 1:1 system to 61% for the 3:1 system. Methacrylate functional group conversion also increased slightly from 92% to 95%.

FIG. 4 shows methacrylate functional group conversion utilizing a methacrylate-thiol-ene system with EBPADMA/PETMP:TMPTN, in a 70/30 weight percent of methacrylate (EBPADMA) to thiol:ene (PETMP:TMPTN). The 1:1; 2:1 and 3:1 ratios represented the molar ratio of thiol (PETMP) to ene (TMPTN) functional groups. The EBPADMA/PETMP:TMPTN system also exhibited increased methacrylate functional group conversion as the thiol-ene ratio and content were increased. Norbornene functional group conversions were not resolvable. Kinetic results in FIGS. 2-4 demonstrated near equivalent polymerization rates for all of the systems that were evaluated.

Table 1 shows the methacrylate-thiol-ene systems all exhibit increased functional group conversion relative to the control dimethacrylate systems. The off-stoichiometric systems contained the same overall weight percent of thiol-ene resin, but the molar ratio of thiol to ene functional groups was 3:2, 2:1, or 3:1 rather than the traditional 1:1 molar ratio of thiol to ene functional groups that was optimum for a step growth system. In the EBPADMA/PETMP:TATATO 60/40 system (60 wt % methacrylate/40 wt % thiol-ene), both 2:1 and 3:1 molar ratios of thiol to ene functional groups were examined and conversion of both methacrylate and ene functional groups was found to be higher than for the 70/30 system. The methacrylate-thiol-ene systems EBPADMA/PETMP:TATATO, and EBPADMA/PETMP:TMPTN exhibited equivalent or greater cure speed with higher overall conversion relative to the dimethacrylate BisGMA/TEGDMA and EBPADMA/TEGDMA control systems.

TABLE 1

Final conversions for BisGMA/TEGDMA, EBPADMA/TEGDMA, EBPADMA/PETMP:TATATO, and EBPADMA/PETMP:TMPTN systems

| Formulation | Wt % Meth/ Thiol:Ene | Thiol:Ene group mol Ratio | Meth Conversion (%) | Ene Conversion (%) |
|---|---|---|---|---|
| BisGMA/TEGDMA 70/30 | — | — | 60 (1) | — |
| EBPADMA/ TEGDMA 70/30 | — | — | 71 (1) | — |
| EBPADMA/ PETMP:TATATO | 70/30 | 1:1 | 92 (1) | 45 (1) |
|  |  | 3:2 | 93 (1) | 53 (1) |
|  |  | 2:1 | 95 (1) | 60 (1) |
|  |  | 3:1 | 94 (1) | 61 (5) |
| EBPADMA/ PETMP:TATATO | 60/40 | 2:1 | 96 (1) | 70 (3) |
|  |  | 3:1 | 98 (1) | 81 (3) |
| EBPADMA/ PETMP:TMPTN | 70/30 | 1:1 | 79 (1) | — |
|  |  | 2:1 | 88 (1) | — |
|  |  | 3:1 | 86 (1) | — |
| EBPADMA/ PETMP:TMPTN | 60/40 | 2:1 | 88 (1) | — |

Example 2

Flexural Modulus and Strength

Methacrylate conversion and mechanical properties of cured resins were tested for methacrylate-thiol-ene, methacrylate-thiol resin systems and dimethacrylate control resins when subjected to identical curing conditions. Relative monomer amounts are shown in Table 2 for each sample. All samples contained 0.3 wt % Irgacure 819, 0.035 wt % Q1301, and were irradiated at 29 mW/cm$^2$ with a 400-500 nm filter for 150 seconds.

Results for flexural modulus and strength for methacrylate, methacrylate-thiol, and methacrylate-thiol-ene systems are shown in Table 2. The EBPADMA/PETMP 80/20 system exhibited an equivalent flexural modulus to BisGMA/TEGDMA and a slightly increased flexural modulus relative to EBPADMA/TEGDMA. The flexural strength is slightly reduced relative to both control systems. Increasing the PETMP content to 25 percent resulted in a decrease in both flexural modulus and strength. The EBPADMA/PETMP:TA- TATO system with a 1:1 thiol:ene stoichiometry exhibited equivalent flexural modulus and strength relative to the EBPADMA/TEGDMA control resin. Increasing the thiol:ene stoichiometry in the 70/30 EBPADMA/PETMP:TA-TATO system did not have a significant effect on the flexural modulus and slightly reduces the flexural strength. Increasing the thiol-ene content to 40% (EBPADMA/PETMP:TATATO 60/40) significantly reduced both flexural modulus and flexural strength for the 2:1 system and results in dramatic reductions for the 3:1 system. The EBPADMA/PETMP:TMPTN 70/30 system with 1:1 thiol:ene stoichiometry exhibited equivalent flexural modulus and strength relative to the Bis-GMA/TEGDMA control resin. Increasing the thiol:ene ratio did not have a statistically significant effect on the flexural modulus and slightly reduces the flexural strength. Increasing the thiol-ene content to 40% (EBPADMA/PETMP:TMPTN 60/40, 2:1) resulted in a system with an equivalent flexural modulus with a slightly reduced flexural strength relative to EBPADMA/TEGDMA.

Example 3

Shrinkage Stress

Various resin system samples were subjected to identical curing conditions with a 400-500 nm filter and 29 mW/cm$^2$ measured by radiometer through 6 mm glass rods. Shrinkage stress of cured resins was measured for methacrylate-thiolene, methacrylate/thiol and dimethacrylate control resins when subjected to identical curing conditions.

Results for shrinkage stress and methacrylate conversion are shown in Table 4. The irradiation intensity for shrinkage stress is measured through the tip of 6 mm glass rods. As such, the actual irradiation intensity is greater than the measured intensity and the samples achieve higher conversion than for flexural or kinetic measurements. The EBPADMA/PETMP systems both exhibited reduced shrinkage stress relative to

TABLE 2

Conversion and flexural modulus and strength data for methacrylate-thiolene and methacrylate-thiol systems and methacrylate control systems

| Formulation Monomers | Methacrylate/Thiol:Ene Wt Ratio | Thiol:Ene Molar Ratio | Methacrylate Conversion (%) | Flexural Modulus (GPa) | Flexural Strength (MPa) |
|---|---|---|---|---|---|
| BisGMA/TEGDMA | 100/0 | — | 58 (1) | 2.0 (0.1) | 84 (1) |
| EBPADMA/TEGDMA | 100/0 | — | 71 (1) | 1.7 (0.1) | 71 (2) |
| EBPADMA/PETMP | 80/20 | 1:0 | 86 (1) | 2.1 (0.1) | 69 (2) |
| EBPADMA/PETMP | 75/25 | 1:0 | 93 (1) | 1.5 (0.1) | 53 (1) |
| EBPADMA/PETMP:TATATO | 70/30 | 1:1 | 72 (1) | 1.8 (0.1) | 71 (3) |
|  |  | 3:2 | 79 (1) | 1.7 (0.1) | 67 (4) |
|  |  | 2:1 | 82 (1) | 1.6 (0.2) | 62 (4) |
|  |  | 3:1 | 86 (1) | 1.6 (0.2) | 57 (2) |
| EBPADMA/PETMP:TATATO | 60/40 | 2:1 | 87 (1) | 1.2 (0.3) | 45 (3) |
|  |  | 3:1 | 93 (1) | 0.4 (0.1) | 24 (2) |
| EBPADMA/PETMP:TMPTN | 70/30 | 1:1 | 73 (1) | 2.0 (0.2) | 79 (5) |
|  |  | 2:1 | 81 (1) | 1.7 (0.1) | 69 (1) |
|  |  | 3:1 | 81 (1) | 1.9 (0.2) | 64 (2) |
| EBPADMA/PETMP:TMPTN | 60/40 | 2:1 | 84 (1) | 1.8 (0.1) | 64 (2) |

Figure 5:
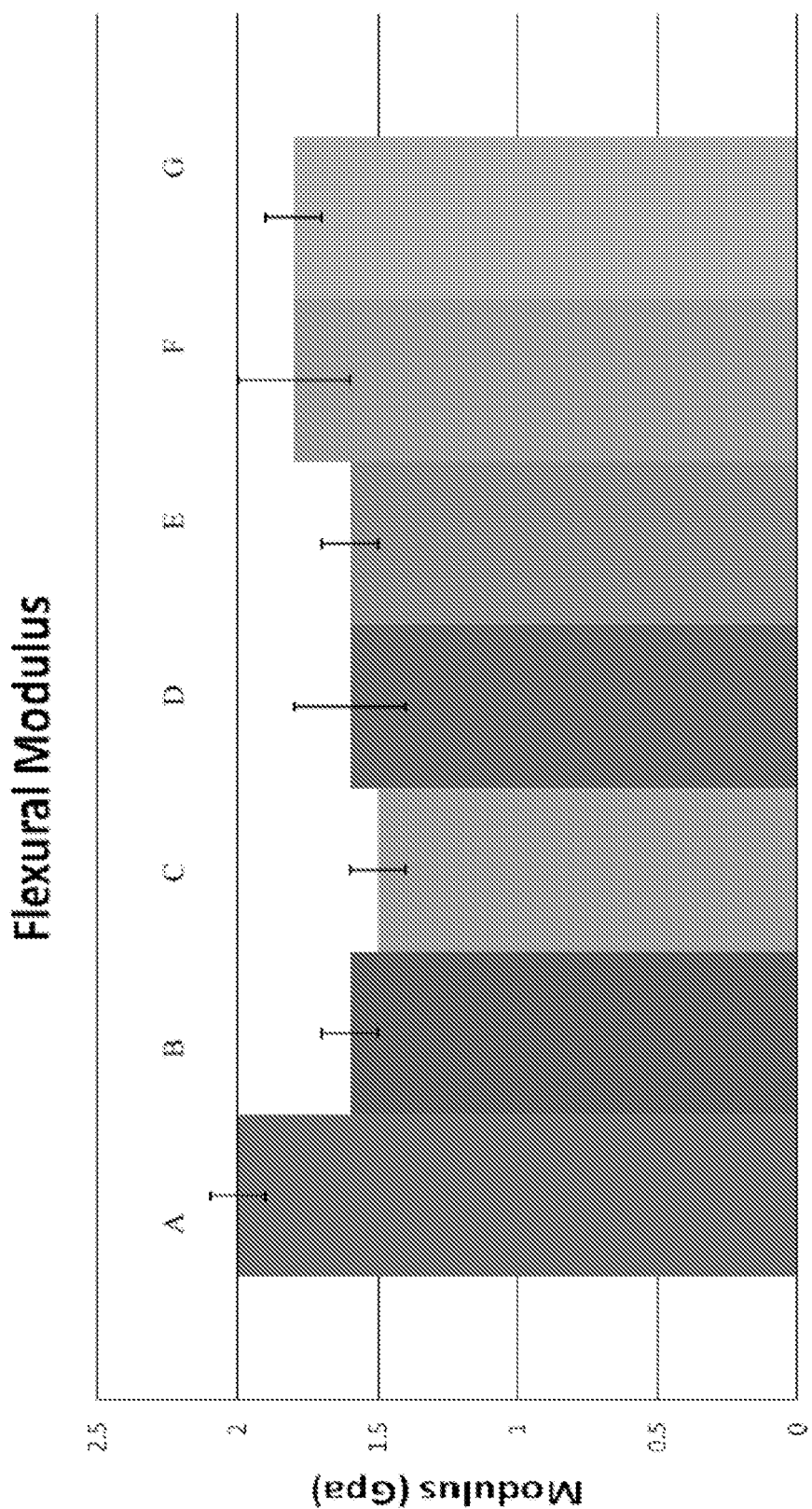
FIG. 5 illustrates Flexural Modulus of two methacrylate control resin systems (A, B), a methacrylate/thiol resin system (C), and four methacrylate/thiol/ene resin systems after photopolymerization. Formulations A-G are illustrated in Table 3.
Figure 6:
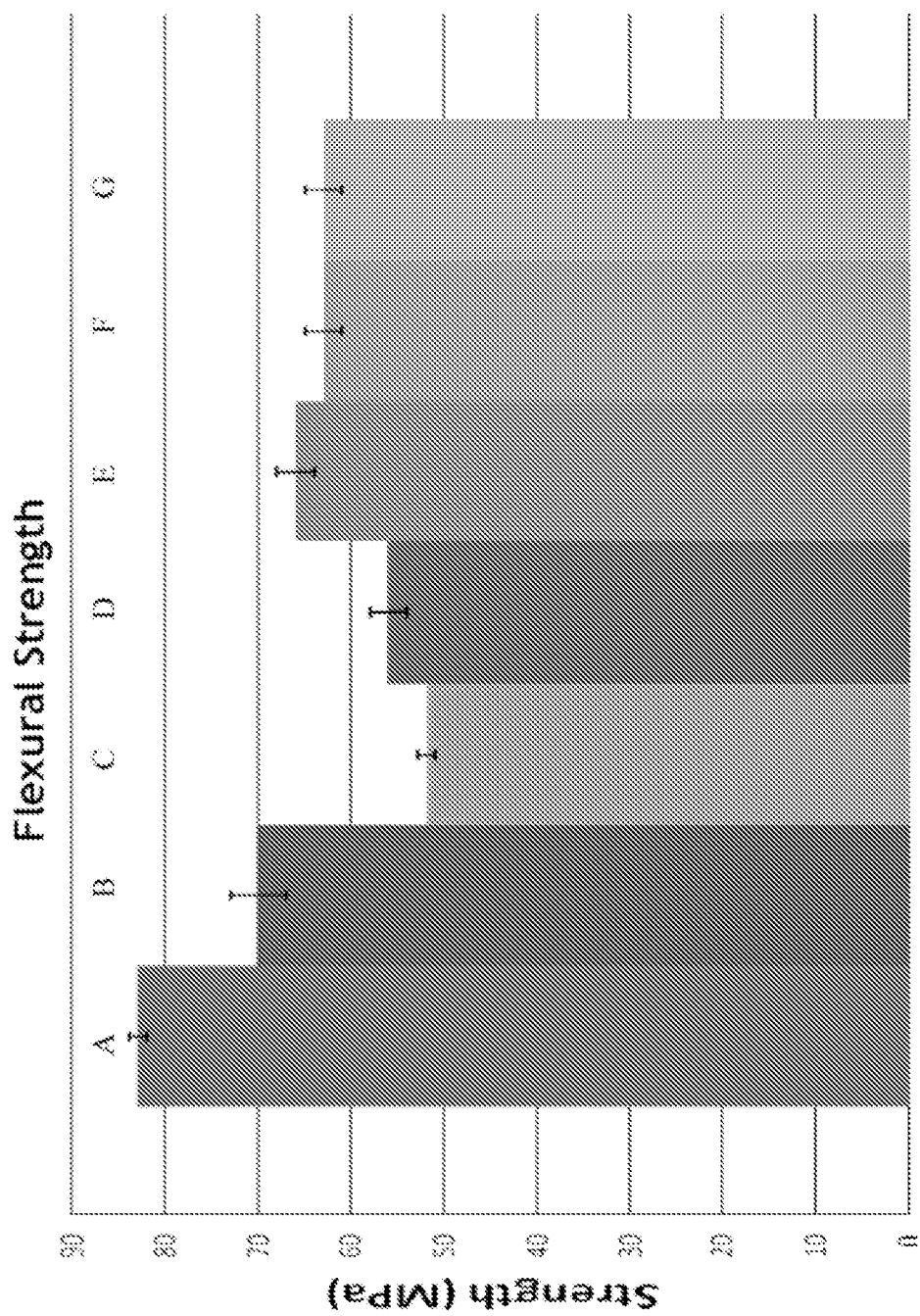
FIG. 6 illustrates Flexural Strength of two methacrylate control resin systems (A, B), a methacrylate/thiol resin system (C), and four methacrylate/thiol/ene resin systems after photopolymerization. Formulations A-G are illustrated in Table 3.

Flexural strength and flexural modulus for several systems is shown graphically in FIG. 4 and FIG. 5, respectively. System A and B represent control methacrylate systems, system C is a methacrylate/thiol system, and systems D-G are methacrylate-thiol-ene systems. Monomers utilized in each resin system are shown in Table 3. Methacrylate-thiol-ene systems exhibited flexural strength and flexural modulus properties approaching those of the methacrylate control systems.

TABLE 3

Resin systems used in flexural strength and modulus experiments illustrated in FIGS. 4 and 5

| System | Monomers | Weight Ratio | Thiol:ene mol ratio |
|---|---|---|---|
| A | BisGMA/TEGMA | 70/30 | NA |
| B | EBPADMA/TEGDMA | 70/30 | NA |
| C | EBPADMA/PETMP | 75/25 | NA |
| D | EBPADMA/PETMP:TATATO | 70/30 | 3:1 |
| E | EBPADMA/PETMP:TMPTN | 70/30 | 2:1 |
| F | EBPADMA/PETMP:TMPTN | 70/30 | 3:1 |
| G | EBPADMA/PETMP:TMPTN | 60/40 | 3:1 | the control resins with stress decreasing with increased thiol content. The EBPADMA/PETMP:TATATO 70/30 systems all exhibit reduced shrinkage stress as compared to the control resins. As the thiol to ene functional group ratio is increased from 1:1 to 3:1 the shrinkage stress is further reduced from 2.1 to 1.4 MPa. The EBPADMA/PETMP:TATATO 60/40 systems exhibit even greater reductions in shrinkage stress than the 70/30 systems. However, these unfilled resin systems also exhibit significant reductions in flexural modulus and strength (Table 2). The EBPADMA/PETMP:TMPTN systems also exhibit reduced shrinkage stress relative to the control resins. For the 70/30 systems, the shrinkage stress ranges from 1.8 to 1.4 MPa as the thiol to ene functional group ratio increases from 1:1 to 3:1. The EBPADMA/PETMP:TMPTN 60/40 system with a 2:1 ratio of thiol to norbornene functional groups exhibits the lowest shrinkage stress (for a system without a significant reduction in flexural modulus and strength) at 1.0 MPa.

Figure 7:
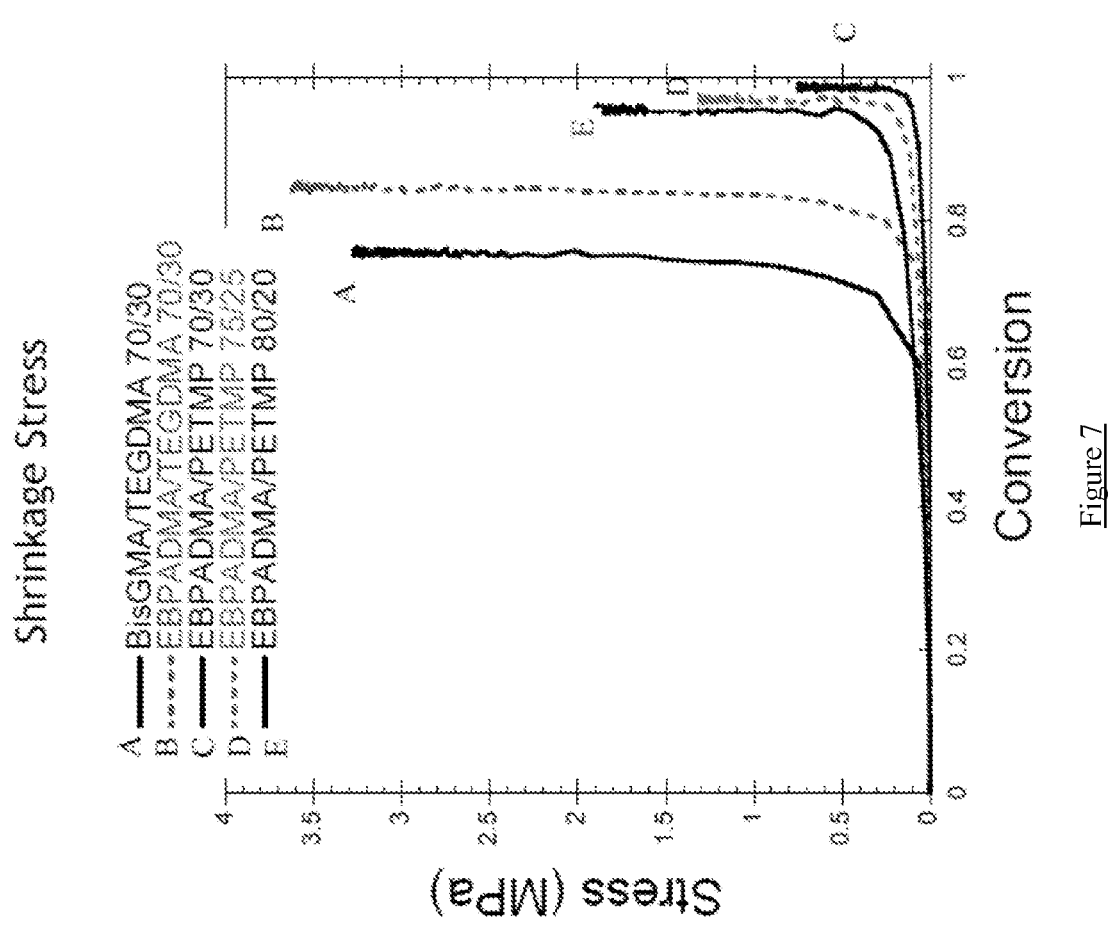
FIG. 7 illustrates shrinkage stress and methacrylate conversion for control methacrylate and methacrylate/thiol systems upon polymerization.
Figure 8:
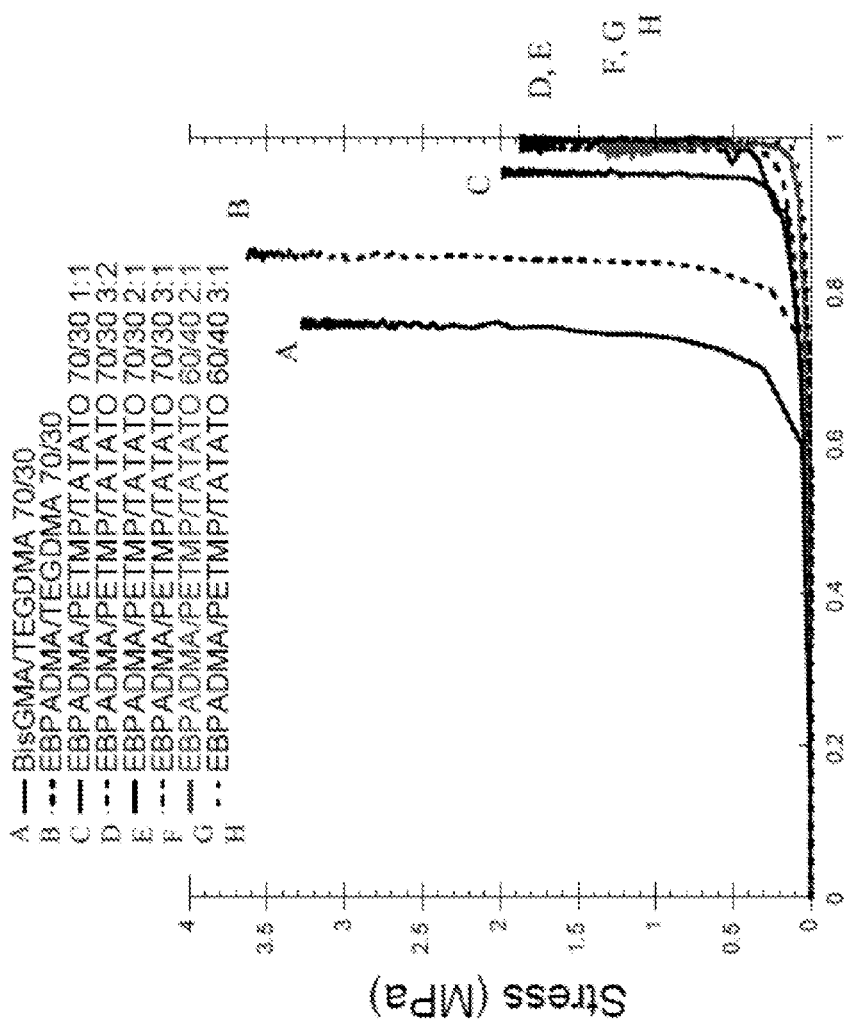
FIG. 8 illustrates shrinkage stress and methacrylate conversion for various EBPADMA/PETMP/TATATO resin systems compared to dimethacrylate control systems.
Figure 9:
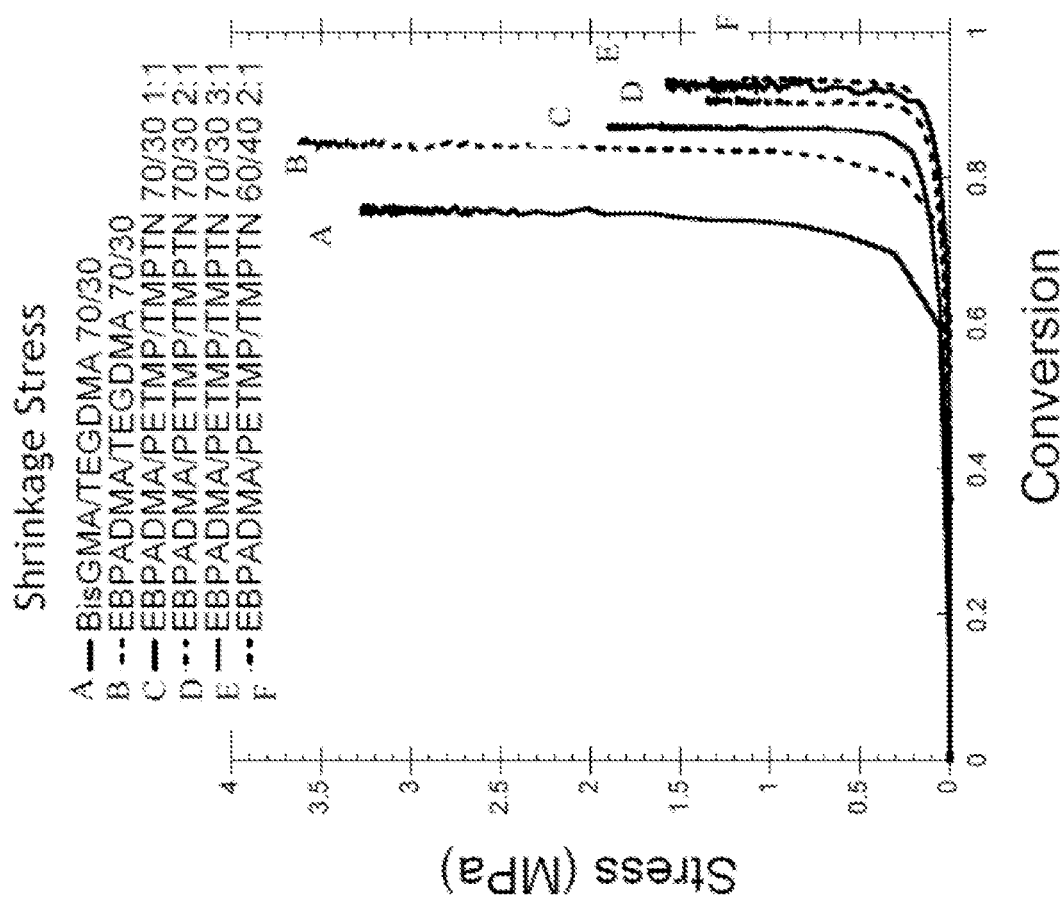
FIG. 9 illustrates shrinkage stress and methacrylate conversion for various EBPADMA/PETMP/TMPTN resin systems compared to dimethacrylate control systems.

Results for shrinkage stress and methacrylate conversion for dimethacrylate control resins and methacrylate/thiol systems are graphically illustrated in FIG. 7. Results for shrinkage stress and methacrylate conversion for various methacrylate-thiol-ene systems compared to dimethacrylate control systems are shown in FIGS. 8 and 9.

TABLE 4

Polymerization shrinkage stress and functional group conversion

| Formulation | Methacrylate/Thiol:Ene Wt Ratio | Thiol:Ene Mol Ratio | Methacrylate Conversion (%) | Shrinkage Stress (MPa) |
|---|---|---|---|---|
| BisGMA/TEGDMA | 70/30 | — | 73 (5) | 3.3 (0.4) |
| EBPADMA/TEGDMA | 70/30 | — | 82 (2) | 3.8 (0.2) |
| EBPADMA/PETMP | 80/20 | 1:0 | 97 (1) | 1.9 (0.2) |
|  | 75/25 | 1:0 | 98 (1) | 1.4 (0.2) |
| EBPADMA/PETMP:TATATO | 70/30 | 1:1 | 86 (1) | 2.1 (0.1) |
|  |  | 3:2 | 94 (1) | 2.0 (0.2) |
|  |  | 2:1 | 96 (1) | 1.9 (0.1) |
|  |  | 3:1 | 98 (1) | 1.4 (0.1) |
| EBPADMA/PETMP:TATATO | 60/40 | 2:1 | 97 (1) | 1.3 (0.1) |
|  |  | 3:1 | 99 (1) | 1.0 (0.1) |
| EBPADMA/PETMP:TMPTN | 70/30 | 1:1 | 87 (1) | 1.8 (0.1) |
|  |  | 2:1 | 90 (1) | 1.4 (0.1) |
|  |  | 3:1 | 92 (2) | 1.5 (0.1) |
| EBPADMA/PETMP:TMPTN | 60/40 | 2:1 | 94 (1) | 1.0 (0.1) |

Example 4

Methacrylate-Thiol-Ene Filled Composites as Dental Restorative

Materials

Various methacrylate-thiol-ene systems were prepared and evaluated relative to dimethacrylate controls. The BisGMA/TEGDMA and EBPADMA/TEGDMA control resins were 70/30 weight percent mixtures. The EBPADMA/PETMP-TATATO resins also contained 70 percent methacrylate (EBPADMA) by weight. The PETMP and TATATO were included at varying stoichiometric ratios: 1:1, 2:1, and 3:1. Each resin included 0.035 wt % Q1301 and 0.3 wt % Irgacure 819. The resins were filled with 72.5 wt % fillers that were 90% Schott 0.4 μm glass and 10 wt % aerosol OX-50. The composites were mixed with a Flacktek Speedmixer (DAC 150 FVZ, Flacktek Inc, Landrum S.C.). Photocuring was performed with a Maxima Pure Power dental lamp.

The methacrylate-thiol-ene systems were evaluated and compared to dimethacrylate controls. In both cases the primary component (70 wt %) was the dimethacrylate and the reactive diluent was a thiol-ene component. For the thiol-ene component, 1:1, 2:1, and 3:1 stoichiometric ratios of thiol to ene functional groups were evaluated in otherwise equivalent composites.

All resins systems were filled to same consistency with inorganic glass filler. The consistency was based on a method in which 3.5 kg of weight is placed on a sample of consistent size for 3 minutes and produces a flattened sample with a diameter of, in this case, 31 mm. This consistency value was chosen in order to make the composites clinically relevant in terms of handling. The methacrylate-thiol-ene resins contain approximately 72.5 wt % inorganic glass filler. The control resins are filled with 73.5 wt % for BisGMA/TEGDMA and 76 wt % for EBPADMA/TEGDMA.

Depth of Cure

A cylindrical mold 6 mm long and 4 mm in diameter was filled with the composite resin and cured for 20 seconds from one end. The uncured material was then removed and the cured specimen was measured in five locations with a micrometer accurate to 0.01 mm and these values were averaged. The averaged value was then divided by two to obtain the depth of cure. The procedure was performed according to ISO 4049-7.10, incorporated herein by reference.

Flexural Strength and Modulus

Six molds were prepared in the dimension 2 mm×2 mm×25 mm and were stored in 37±1° C. distilled water for 24±2 hours. The molds were then broken using a universal materials testing machine (Instron 4411, Instron, Norwood Mass.). The procedure was performed according to ISO 4049-7.11, incorporated herein by reference.

Fourier Transform Infrared Spectroscopy (FTIR)

Experiments were utilized for functional group conversion and conducted in the near infrared (7000-4000 $cm^{-1}$) using a Nicolet 6700 FTIR spectrometer (Madison, Wis.) with a XT-KBr beam splitter and a DTGS KBr detector. Samples were placed between two thin plastic films and two glass slides with a sample thickness of 2 mm. Functional group conversions were monitored utilizing the methacrylate absorption at 6,164 $cm^{-1}$ and the allyl ether absorption peak at 6,132 $cm^{-1}$. A Gaussian fitting peak deconvolution method was utilized to determine the individual functional group conversion. For each system, six trials were performed.

Volumetric Shrinkage

A small sample of material was placed on the detector of a linometer (ACTA, Amsterdam) and cured for 40 seconds. The linear shrinkage was then recorded for an additional ten minutes and the linear shrinkage value at the end of testing was multiplied by three to approximate volumetric shrinkage of the composite. A minimum of three trials were conducted for each material.

Polymerization Stress

A tensometer (American Dental Association Health Foundation) detected stress development using cantilever beam theory. A cylindrical sample 6 mm in diameter and 1.5 mm thick was irradiated for 40 seconds and the stress profile was monitored for an additional 20 minutes. A minimum of three trials were conducted.

Water Absorption and Solubility

Five cylindrical molds were prepared 15 mm in diameter and 1 mm thick. Specimens were maintained in a dessicator at 37±1° C. until a constant weight is recorded (ml). The physical dimensions are recorded and the specimens were then immersed in distilled water maintained at 37±1° C. for seven days. The molds were then blotted dry and air dried for 15 seconds before being weighed (m2). The specimens were then returned to the dessicator at 37±1° C. until a constant weight is again reached (m3). Water sorption (Wsp) and water solubility (Ws1) were then calculated according to equations 1 and 2.

$$W_{zp} = \frac{m2 - m3}{V} \quad \text{Equation 1}$$

$$W_{sp} = \frac{m1 - m3}{V}. \quad \text{Equation 2}$$

V is equal to the volume of each specimen, calculated from the dimensions recorded. The procedure was performed according to ISO 4049-7.12, incorporated herein by reference.

Mechanical Properties

Flexural strength and modulus were evaluated for each of the composite systems. Results are given in Table 5. All of the systems exhibited higher flexural strength than the control composites. The flexural modulus was highest for the 1:1 system and decreases for the 2:1 and 3:1 systems. The flexural modulus was higher for all three of the ternary methacrylate/thiol-ene systems than the control systems.

TABLE 5

Flexural properties of control and experimental systems

| Formulation | Thiol:Ene Ratio | Flexural Strength (MPa) | Flexural Modulus (GPa) |
|---|---|---|---|
| BisGMA/TEGDMA | / | 102 (7) | 7.2 (0.7) |
| EBPADMA/TEGDMA | / | 114 (5) | 7.7 (0.3) |
| EBPADMA/PETMP:TATATO | 1:1 | 145 (11) | 9.2 (0.9) |
| EBPADMA/PETMP:TATATO | 2:1 | 146 (8) | 8.8 (0.8) |
| EBPADMA/PETMP:TATATO | 3:1 | 150 (9) | 8.2 (1.0) |

Depth of Cure

The calculated depth of cure for each material after 20 seconds of light curing is shown in Table 6.

TABLE 6

Depth of cure after 20 sec light curing

| Formulation | Thiol:Ene Ratio | Depth of Cure (mm) |
|---|---|---|
| BisGMA/TEGDMA | / | 2.15 (0.04) |
| EBPADMA/TEGDMA | / | 2.26 (0.03) |
| EBPADMA/PETMP:TATATO | 1:1 | 2.53 (0.04) |
| EBPADMA/PETMP:TATATO | 2:1 | 2.62 (0.03) |
| EBPADMA/PETMP:TATATO | 3:1 | 2.63 (0.06) |

The depth of cure was increased over the control systems for the ternary methacrylate/thiol-ene systems. There was not much significant difference between the depth of cure values for the three experimental systems.

C=C Conversion

The methacrylate function group conversion of the materials was measured for each of the samples tested for flexural modulus and strength. Table 7 shows the methacrylate and allyl ether conversion. The methacrylate conversion for the ternary systems was increased over the conversion for the methacrylate controls. The allyl ether conversion increased significantly in the ternary systems as the ratio of thiol-to-ene is increased in favor of the thiol monomer.

TABLE 7

Functional group conversion

| Formulation | Thiol:Ene Ratio | Methacrylate Conversion (%) | Ene Conversion (%) |
|---|---|---|---|
| BisGMA/TEGDMA | / | 54 (1) | / |
| EBPADMA/TEGDMA | / | 59 (1) | / |
| EBPADMA/PETMP:TATATO | 1:1 | 69 (1) | 17 (2) |
| EBPADMA/PETMP:TATATO | 2:1 | 72 (2) | 29 (2) |
| EBPADMA/PETMP:TATATO | 3:1 | 74 (1) | 35 (3) |

Volumetric Shrinkage

The shrinkage determined with the linometer for each material is shown in Table 8. The volume shrinkage for the 1:1 systems was not statistically different from the controls, but as the ratio of thiol-to-ene is increased, the shrinkage decreases.

TABLE 8

Volumetric shrinkage

| Formulation | Thiol:Ene Ratio | Volumetric Shrinkage (%) |
|---|---|---|
| BisGMA/TEGDMA | / | 2.35 (0.03) |
| EBPADMA/TEGDMA | / | 2.49 (0.08) |
| EBPADMA/PETMP:TATATO | 1:1 | 2.27 (0.10) |
| EBPADMA/PETMP:TATATO | 2:1 | 2.03 (0.07) |
| EBPADMA/PETMP:TATATO | 3:1 | 1.84 (0.17) |

Shrinkage Stress

The polymerization stress for each system is shown in Table 9. The ternary methacrylate/thiol-ene systems showed approximately a 20-30% reduction in shrinkage stress compared to the control systems.

TABLE 9

Shrinkage stress

| Formulation | Thiol:Ene Ratio | Shrinkage Stress (MPa) |
|---|---|---|
| BisGMA/TEGDMA | 1 | 2.19 (0.04) |
| EBPADMA/TEGDMA | / | 2.28 (0.04) |
| EBPADMA/PETMP:TATATO | 1:1 | 1.70 (0.11) |
| EBPADMA/PETMP:TATATO | 2:1 | 1.78 (0.16) |
| EBPADMA/PETMP:TATATO | 3:1 | 1.52 (0.25) |

Water Sorption and Solubility

Table 10 shows the results for the water sorption and solubility of the materials. There was a significant decrease in both water sorption and solubility for the thiol-ene systems compared to the BisGMA/TEGDMA control and a slight decrease in both properties from the EBPADMA/TEGDMA control. There did not seem to be a significant trend in the properties when the amount of thiol in the ternary systems is increased.

TABLE 10

Water sorption and solubility

| Formulation | Thiol:Ene Ratio | Water Sorption ($\mu g/mm^3$) | Water Solubility ($\mu g/mm^3$) |
|---|---|---|---|
| BisGMA:TEGDMA | / | 30.3 (0.6) | 5.1 (0.4) |
| EBPADMA/TEGDMA | / | 15.2 (0.7) | 3.1 (1.2) |
| EBPADMA/PETMP:TATATO | 1:1 | 13.5 (1.6) | 0.3 (0.8) |
| EBPADMA/PETMP:TATATO | 2:1 | 11.9 (1.3) | −0.9 (0.9) |
| EBPADMA/PETMP:TATATO | 3:1 | 13 (1.2) | −0.8 (0.5) |

Example 5

Other Filler Compositions for Methacrylate-Thiol-Ene Filled Composites

Staring with a resin composition comprising methacrylate/thiol:ene at a 60/40 wt ratio of methacrylate to thiol-ene component and a 2:1 molar ratio of thiol to ene functional groups. Two methacrylate-thiol-ene systems were evaluated: EBPADMA/PETMP:TATATO (alpha formulation in Figures) and EBPDMA/PETMP:TMPTN (beta formulation in Figures) resins were utilized in the following filler experiments. Filler powders were varied according to the following protocol. All formulations contain a combined 95 wt % of Schott 0.5 micron barium glass and Ytterbium 40 nm nanoglass and nanoclusters. All formulations also contained a combined 5 wt % of Aerosil and Cabosil fumed silica fillers. All tested combinations are shown in Table 11.

TABLE 11

Fillers in methacrylate-thiol-ene composite

| | wt % of powder | | | | |
|---|---|---|---|---|---|
| Formulation | schott | ytterbium | aerosil | cabosil | wt % filled |
| A1 | 80 | 15 | 5.0 | 0.0 | 76.8 |
| A2 | 80 | 15 | 0.0 | 5.0 | 75.9 |
| A3 | 80 | 15 | 2.5 | 2.5 | 76.1 |
| B1 | 85 | 10 | 5.0 | 0.0 | 76.1 |
| B2 | 85 | 10 | 0.0 | 5.0 | 74.5 |
| B3 | 85 | 10 | 2.5 | 2.5 | 75.8 |
| C1 | 90 | 5.0 | 5.0 | 0.0 | 76.5 |
| C2 | 90 | 5.0 | 0.0 | 5.0 | 75.8 |
| C3 | 90 | 5.0 | 2.5 | 2.5 | 75.2 |

The composites were filled to attain a certain consistency, but all had similar filling percentages. The composites were compounded as follows. Mixing was performed in a Flacktek centrifugal mixer. Powders were mixed together in a bag and added slowly to a mixing jar containing the resin solution. Approximately ¼ of the powders were added and then mixed, another ¼ were added and mixed, another ¼ were added and mixed. The rest of the powders were added in small portions in order to achieve the desired consistency and not make the composite too thick.

The composites were cured with a dental lamp: visible light (400-500 nm) at about 400 mW/cm$^2$. The cure times were different for each test as follows:
 a. Depth of cure—20 sec;
 b. Microhardness, Flexural, Compressive, DTS, Conversion—40 sec each side; and
 c. Volume Shrinkage—40 sec.

Figure 10:
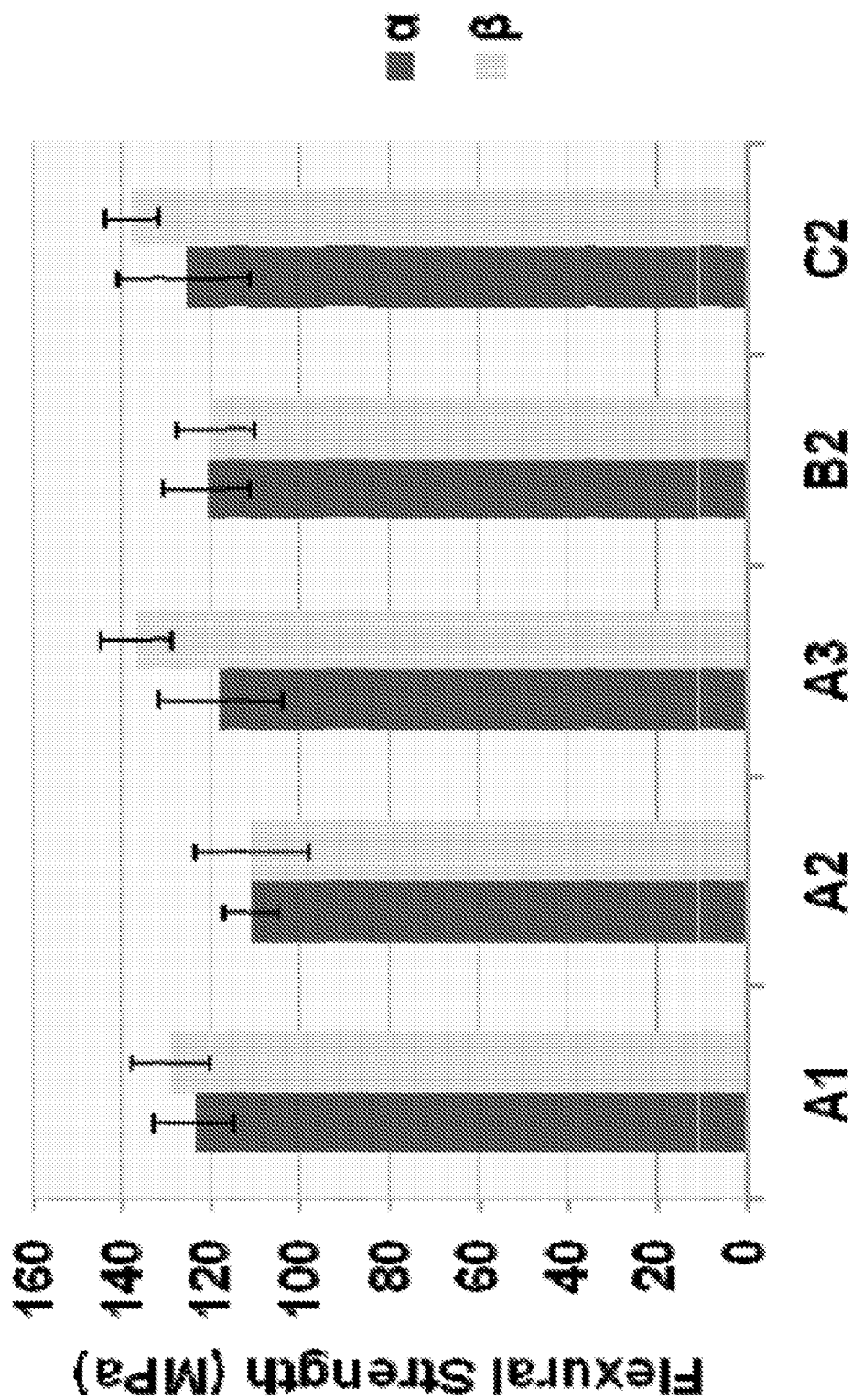
FIG. 10 illustrates flexural strength for two methacrylate-thiol-ene systems with various filler formulations from Example 5.
Figure 11:
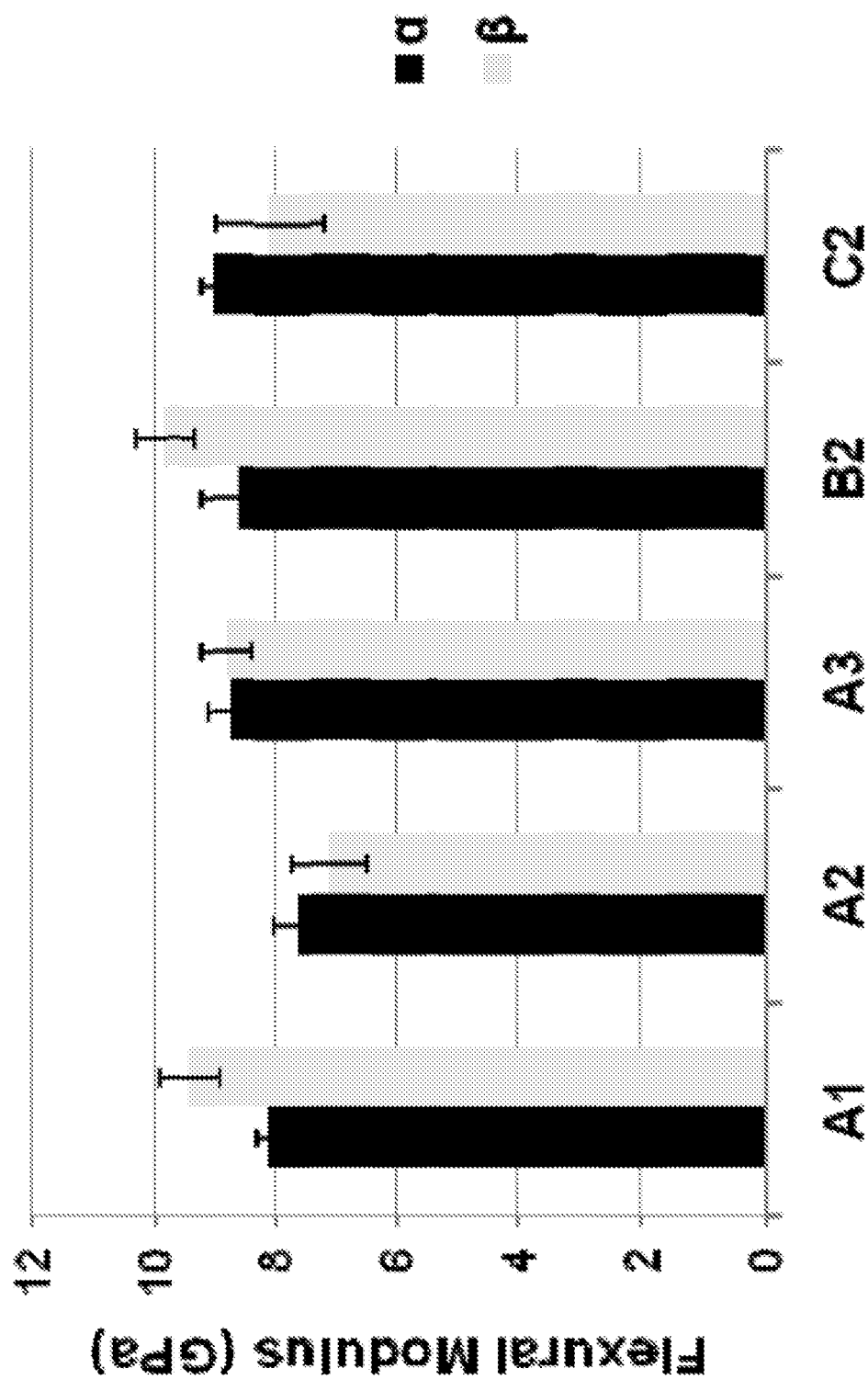
FIG. 11 illustrates flexural modulus for two methacrylate-thiol-ene systems with various filler formulations from Example 5.
Figure 12:
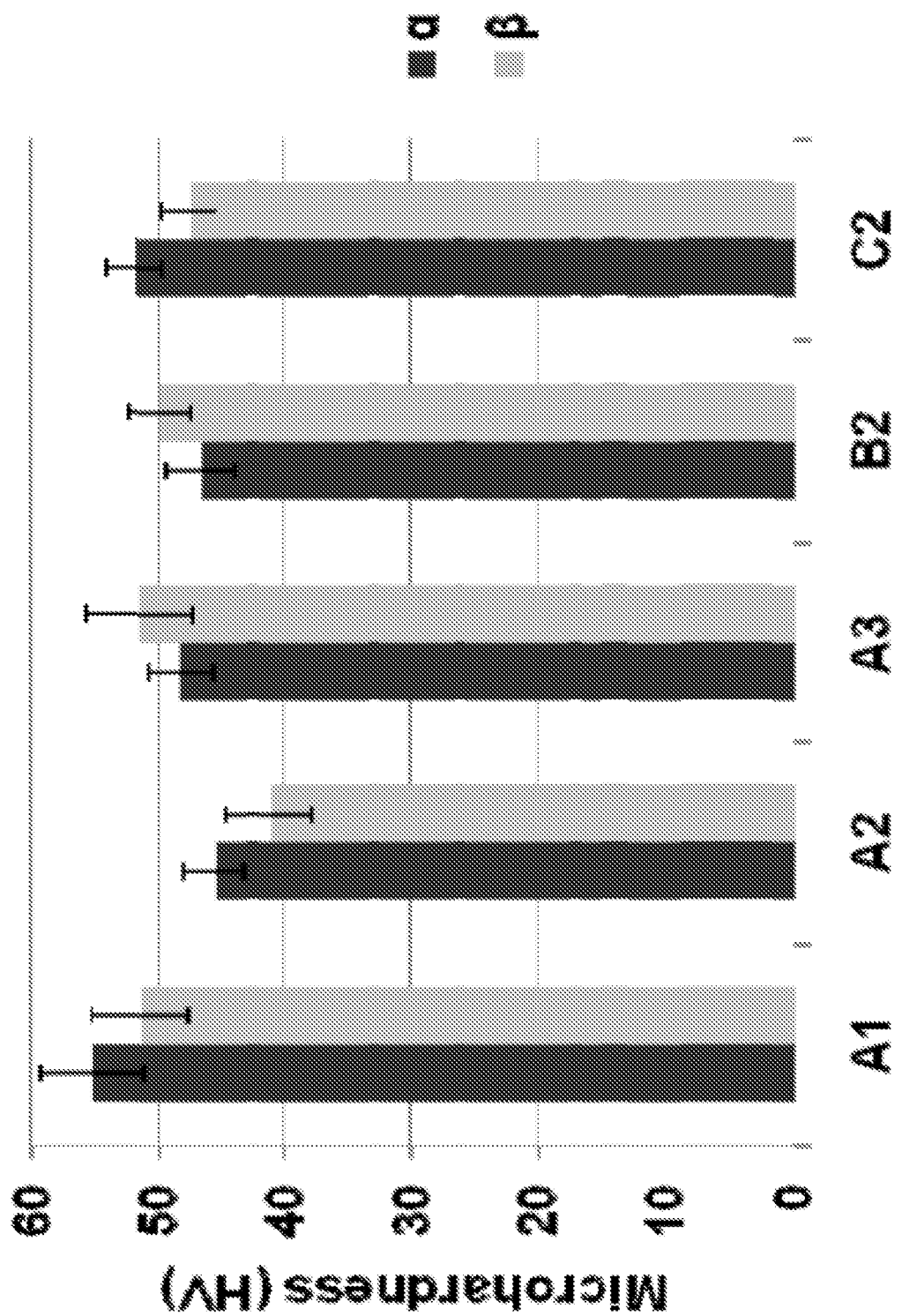
FIG. 12 illustrates microhardness for two methacrylate-thiol-ene systems with various filler formulations from Example 5.

Results for selected EBPADMA/PETMP:TATATO (alpha) and EBPDMA/PETMP:TMPTN (beta) filled cured resins are shown in FIGS. 10-12. FIG. 10 shows results for flexural strength. There were no statistical differences in flexural strength between filler powder formulations for each resin formulation, or between the resin formulations.

FIG. 11 shows filler formulation A2 exhibited a lower flexural modulus in both resin formulations. There was also a different flexural modulus between resin formulations for the A1 formulation. There was little difference in flexural modulus for A3, B2, C2 for either alpha or beta resin formulation. FIG. 12 shows microhardness results for selected formulations. Although there was some variation in microhardness between different powder formulations, there was no statistical difference between resin formulations with the same powder formulations.

Further data for EBPADMA/PETMP:TATATO (alpha) filled composites at a 60/40 wt ratio of methacrylate to thiol-ene component and a 2:1 molar ratio of thiol to ene functional groups are shown in Tables 12 and 13 below.

TABLE 12

Filler optimization data for EBPADMA/PETMP:TATATO 60/40, 2:1

| Filler | Consistency (3.5 kg, 3 min) | Depth of Cure (mm) | Micro-hardness | Flexural Strength (MPa) | Flexural Modulus (MPa) |
|---|---|---|---|---|---|
| A1 | 22 × 22 | 2.86 | 55.2 (4.0) | 124 (9) | 8094 (176) |
| A2 | 17 × 17 | 2.52 | 45.6 (2.4) | 111 (6) | 7582 (401) |
| B2 | 19 × 20 | 2.24 | 46.7 (2.7) | 118 (10) | 8592 (573) |
| C2 | 18 × 18 | 2.81 | 52.0 (2.2) | 121 (15) | 8972 (183) |
| A3 | 24 × 24 | 2.26 | 48.4 (2.6) | 126 (14) | 8687 (415) |
| B3 | 26 × 26 | 2.07 | 47.3 (1.4) | 155 (8) | 9188 (747) |
| C3 | 25 × 26 | 2.43 | 46.3 (1.4) | 152 (7) | 9525 (318) |
| B1 | 29 × 30 | 2.32 | 51.0 (2.2) | 147 (8) | 9238 (273) |
| C1 | 28 × 28 | 2.63 | 51.2 (2.9) | 141 (11) | 8727 (327) |

TABLE 13

Filler optimization data for EBPADMA/PETMP:TATATO 60/40, 2:1

| | | | C=C Conversion | | |
|---|---|---|---|---|---|
| Filler | Compressive Strength (MPa) | DTS (MPa) | Overall | Methacrylate | Allyl Ether |
| A1 | 299 (22) | 55 (6) | 78 (1) | 83 (1) | 43 (1) |
| A2 | 222 (47) | 50 (3) | 78 (<1) | 83 (<1) | 46 (1) |
| B2 | 293 (34) | 44 (4) | 78 (1) | 83 (1) | 48 (1) |
| C2 | 305 (22) | 53 (5) | 75 (1) | 81 (1) | 45 (3) |
| A3 | 233 (24) | 59 (4) | 79 (1) | 84 (1) | 46 (1) |
| B3 | 339 (30) | 64 (5) | 78 (<1) | 82 (<1) | 51 (1) |
| C3 | 288 (18) | 68 (1) | 78 (<1) | 83 (<1) | 54 (3) |
| B1 | 293 (36) | 62 (4) | 77 (<1) | 81 (1) | 49 (3) |
| C1 | 333 (35) | 54 (3) | 77 (<1) | 81 (1) | 49 (<1) |

Example 6

Biocompatibility Study

In vitro mammalian cell culture studies have been used historically to evaluate cytotoxicity of biomaterials and medical devices (Wilsnack, et al., 1973, Biomat. Med. Dev. & Artif. Organs 1:543-562). A cytotoxicity study was used to evaluate the biocompatibility of a test article extract using an in vitro mammalian cell culture test. This study was based on the requirements of the International Organization for Standardization 10993: Biological Evaluation of Medical Devices, Part 5: in vitro Methods.

Test articles were extracted with single strength Minimal Essential Medium supplemented with 5% serum and 2% antibiotics (1×MEM). Articles were extracted based upon the USP ratio for material thickness greater than or equal to 0.5 mm, a ratio of 60 cm$^2$: 20 mL extraction vehicle. The test and control articles were extracted at 37° C. for 24 hours using 1×MEM to simulate physiological conditions. The test/control article was discarded. The extracts were evaluated in the following assay.

A number of controls were used to evaluate the assay performance. For the Negative Control, high density polyethylene was prepared and a single preparation of the material was extracted using the same conditions as uses for the test article. A Reagent Control was a single aliquot of the extraction vehicle without test material was prepared and treated using the same conditions as described for the test article. A Positive Control of tin stabilized polyvinylchloride, the current NAMSA positive control vehicle, was prepared using same ratio of test article to extraction vehicle.

Mammalian cell culture monolayer, L-929, mouse fibroblast cells, (ECACC Catalog No. 85103115), were used. L-929 cells were propagated and maintained in open wells containing single strength Minimum Essential Medium supplemented with 5% serum and 2% antibiotics (1×MEM) in a gaseous environment of 5% carbon dioxide ($CO_2$). For this study, 10 $cm^2$ wells were seeded, labeled with passage number and date, and incubated at 37° C. in 5% $CO_2$ to obtain sub-confluent monolayers of cells prior to use. Aseptic procedures were used in the handling of the cell cultures following approved NAMSA Standard Operating Procedures.

Each culture well was selected which contained a sub-confluent cell monolayer. The growth medium in triplicate cultures was replaced with 2 mL of the test extract. Similarly, triplicate cultures were replaced with 2 mL of the reagent, negative and positive control extracts. Each well was labeled with the corresponding lab number, replicate number and the dosing date and incubated at 37° C. in 5% $CO_2$ for 48 hours.

Following incubation, the cultures was examined microscopically (100×) to evaluate cellular characteristics and percent lysis. The color of the test medium was observed. Each culture well was evaluated for percent lysis and cellular characteristics using the criteria shown in Table 14 (United States Pharmacopeia, USP 31, National Formulary 26 Ch. 87. Biological Reactivity Tests, in vitro (2008)). The reagent control and the negative control had a reactivity of grade 0 and the positive controls were scored as a grade 3 or 4.

TABLE 14

USP cytotoxicity scoring

| Grade | Reactivity | Conditions of all Cultures |
|---|---|---|
| 0 | None | Discrete intracytoplasmic granules: no cell lysis |
| 1 | Slight | Not more than 20% of the cells are round, loosely attached, and without intracytoplasmic granules; occasional lysed cells are present |
| 2 | Mild | Not more than 50% of the cells are round and devoid of intracytoplasmic granules: no extensive cell lysis and empty arena between cells |
| 3 | Moderate | Not more than 70% of the cell layers contain rounded cells or are lysed |
| 4 | Severe | Nearly complete destruction of the cell layers |

The following samples were tested in this assay. The methacrylate-thiol-resin resin systems and composite systems (filled resin systems) were not considered orally toxic based on the test conditions.

TABLE 15

Cytotoxicity data for resin and composite systems

| Resin Systems | Grade |
|---|---|
| BisGMA/TEGDMA (70/30) | 3 |
| EBPADMA/PETMP:TATATO (80/20) | 0 |
| EBPADMA/PETMP:TMPTN (70/30) | 0 |
| Composite Systems (75 wt % filled) | 0 |
| EBPADMA/PETMP:TATATO (60/40, 2:1) (alpha system) | 0 |
| EBPADMA/PETMP:TMPTN (60/40, 2:1) (beta system) | 0 |

Example 7

Shrinkage Stress

Figure 13:
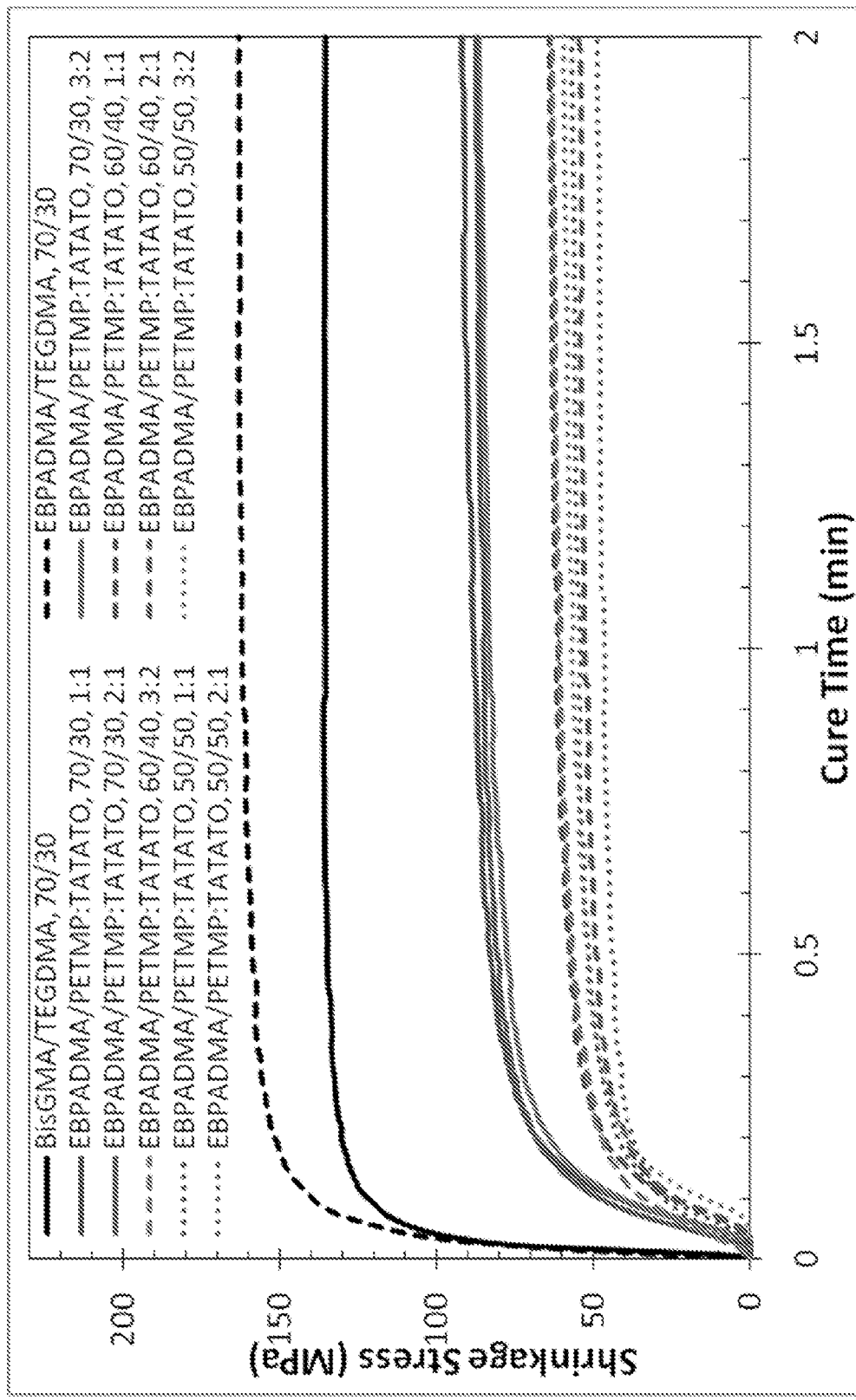
FIG. 13 is a graph illustrating shrinkage stress versus irradiation time for samples cured on a tensometer. Samples contained 0.3 wt % Irgacure 819, 0.035 wt % Q-1301, and were irradiated at 77 mW/cm$^2$ for 300 seconds with a 400-500 nm filter.

A tensometer (American Dental Association Health Foundation) was used to measure stress development. Specimens ~1.5 mm thick were placed between 6 mm diameter glass rods with silane treated ends. The curing light was transmitted through the lower glass rod. Three trials were conducted for each material. The results of this study are illustrated in FIG. 13.

Table 16 illustrates shrinkage stress for samples cured on a tensometer.

Samples contained 0.3 wt % Irgacure 819, 0.035 wt % Q-1301, and were irradiated at 77 mW/$cm^2$ for 300 seconds with a 400-500 nm filter. Values in parenthesis represent standard deviation.

TABLE 16

| Formulation | Final Shrinkage Stress (Mpa) |
|---|---|
| BisGMA/TEGDMA, 70/30 | 150 (10) |
| EBPADMA/TEGDMA, 70/30 | 170 (6) |
| EBPADMA/PETMP:TATATO, 70/30, 1:1 | 98 (3) |
| EBPADMA/PETMP:TATATO, 70/30, 3:2 | 94 (5) |
| EBPADMA/PETMP:TATATO, 70/30, 2:1 | 94 (4) |
| EBPADMA/PETMP:TATATO, 60/40, 1:1 | 70 (5) |
| EBPADMA/PETMP:TATATO, 60/40, 3:2 | 70 (5) |
| EBPADMA/PETMP:TATATO, 60/40, 2:1 | 65 (9) |
| EBPADMA/PETMP:TATATO, 50/50, 1:1 | 63 (4) |
| EBPADMA/PETMP:TATATO, 50/50, 3:2 | 65 (4) |
| EBPADMA/PETMP:TATATO, 50/50, 2:1 | 54 (3) |

Example 8

Volume Shrinkage

A small sample of material was placed on the detector of a linometer (ACTA, Amsterdam) and cured for 600 seconds. The linear shrinkage value at the end of testing was multiplied by three to approximate volumetric shrinkage. Three trials were conducted for each material.

Table 17 illustrates volume shrinkage measured with a linometer. Samples contained 0.3 wt % Irgacure 819, 0.035 wt % Q-1301, and were irradiated at 5 mW/cm2 for 600 seconds with a 320-500 nm filter. Values in parenthesis represent standard deviation.

TABLE 17

| Formulation | Volume Shrinkage (%) |
|---|---|
| BisGMA/TEGDMA 70/30 | 6.3 (0.3) |
| EBPADMA/TEGDMA 70/30 | 6.8 (0.1) |
| EBPADMA/PETMP:TATATO 70/30, 1:1 | 5.4 (0.2) |
| EBPADMA/PETMP:TATATO 70/30, 3:2 | 4.7 (0.1) |
| EBPADMA/PETMP:TATATO 70/30, 2:1 | 4.9 (0.2) |
| EBPADMA/PETMP:TATATO 60/40, 1:1 | 5.5 (0.1) |
| EBPADMA/PETMP:TATATO 60/40, 3:2 | 4.9 (0.1) |
| EBPADMA/PETMP:TATATO 60/40, 2:1 | 4.5 (0.3) |
| EBPADMA/PETMP:TATATO 50/50, 1:1 | 4.6 (0.2) |
| EBPADMA/PETMP:TATATO 50/50, 3:2 | 4.6 (0.1) |
| EBPADMA/PETMP:TATATO 50/50, 2:1 | 4.5 (0.2) |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A photopolymerizable dental restorative composition comprising polymerizable monomers, wherein:
   about 50% to about 70% of the total weight of the polymerizable monomers is a methacrylate monomer, the balance by weight of the polymerizable monomers is a mixture of a thiol monomer and an ene monomer; and, the molar ratio of thiol functional groups from the thiol monomer relative to the ene functional groups from the ene monomer is greater than about 1.5:1.

2. The composition of claim 1, wherein the molar ratio of the thiol functional groups to the ene functional groups is equal to or greater than about 1.75:1.

3. The composition of claim 2, wherein the molar ratio of the thiol functional groups to the ene functional groups is equal to or greater than about 2:1.

4. The composition of claim 1, further comprising a photoinitiator.

5. The composition of claim 4, wherein the photoinitiator comprises a visible light activated photoinitiator, a UV light activated photoinitiator, or a combination thereof.

6. The composition of claim 4, wherein the photoinitiator is selected from the group consisting of (2,4,6-trimethyl benzoyl)phosphine oxide, camphorquinone, bis(eta 5-2,4-cyclopentadien-1-yl)bis[2,6-difluoro-3-(1H-pyrrol-1-yl)phenyl] titanium, 1-hydroxy-cyclohexyl-phenylketone, 2,2-dimethoxy-2-phenylacetophenone, and any combinations thereof.

7. The composition of claim 4, further comprising a polymerization accelerator.

8. The composition of claim 4, further comprising a polymerization inhibitor.

9. The composition of claim 1, further comprising a filler in an amount of up to 90% by weight with respect to the total weight of the filled composition.

10. The composition of claim 9, wherein the filler is about 60 to about 85% by weight with respect to the total weight of the filled composition.

11. The composition of claim 10, wherein about 50% to about 60% of the total weight of the polymerizable monomers is a methacrylate monomer.

12. The composition of claim 10, wherein about 60% to about 70% of the total weight of the polymerizable monomers is a methacrylate monomer.

13. The composition of claim 1, wherein the methacrylate monomer is a dimethacrylate monomer.

14. The composition of claim 13, wherein the methacrylate monomer is selected from the group consisting of ethylene glycoldi(meth)acrylate, ethoxylated bisphenol-A dimethacrylate (EBPADMA), tetraethyleneglycoldi(meth)acrylate (TEGDMA), poly(ethylene glycol)dimethacrylates, the condensation product of bisphenol A and glycidyl methacrylate, 2,2'-bis-[4-(3-methacryloxy-2-hydroxy propoxy)-phenyl]propane (BisGMA), hexanediol di(meth)acrylate, tripropylene glycol di(meth)acrylate, butanediol di(meth)acrylate, neopentyl glycol di(meth)acrylate, diethylene glycol di(meth)acrylate, triethylene glycol di(meth)acrylate, dipropylene glycol di(meth)acrylate, allyl(meth)acrylate, and any combinations thereof.

15. The composition of claim 14, wherein the methacrylate monomer is ethoxylated bisphenol-A dimethacrylate (EBPADMA) or 2,2'-bis-[4-(3-methacryloxy-2-hydroxy propoxy)-phenyl]propane (BisGMA).

16. The composition of claim 1, wherein the thiol monomer is selected from the group consisting of pentaerythritol tetramercaptopropionate (PETMP), 1-octanethiol, butyl 3-mercaptopropionate, 2,4,6-trioxo-1,3,5-triazina-triy(triethyl-tris (3-mercapto propionate), 1,6-hexanedithiol, 2,5-dimercaptomethyl-1,4-dithiane, pentaerythritol tetramercaptoacetate, trimethylolpropane trimercaptoacetate, 2,3-dimercapto-1-propanol, 2-mercaptoethylsulfide, 2,3-(dimercaptoethylthio)-1-mercaptopropane, 1,2,3-trimercaptopropane, toluenedithiol, xylylenedithiol, 1,8-octanedithiol, 1-hexanethiol and trimethylolpropane tris(3-mercaptopropionate), glycol dimercaptopropionate, and any combinations thereof.

17. The composition of claim 16, wherein the thiol monomer is pentaerythritol tetramercaptopropionate (PETMP).

18. The composition of claim 1, wherein the ene monomer comprises two or more ene functional groups.

19. The composition of claim 16, wherein the ene monomer is selected from the group consisting of triallyl-1,3,5-triazine-2,4,6-trione (TATATO), triethyleneglycol divinyl ether (TEGDVE), trimethylolpropane diallyl ether, dodecyl vinyl ether (DDVE), 1,6-heptadiyne, 1,7-octadiyne, bis-2,2-[4-(2-[norborn-2-ene-5-carboxylate]ethoxy)phenyl]propane (BPAEDN), 1,6-hexanediol di-(endo,exo-norborn-2-ene-5-carboxylate) (HDDN), trimethylolpropane tri-(norborn-2-ene-5-carboxylate) (TMPTN), pentaerythritoltri-(norborn-2-ene-5-carboxylate) (PTN3), pentaerythritol tetra-(norborn-2-ene-5-carboxylate) (PTN4), tricyclodecane dimethanol di-(endo, exo-norborn-2-ene-5-carboxylate) (TCDMDN), di(trimethylolpropane)tetra-(norborn-2-ene-5-carboxylate) (DTMPTN), and any combinations thereof.

20. The composition of claim 19, wherein the ene monomer is selected from the group consisting of triallyl-1,3,5-triazine-2,4,6-trione (TATATO), trimethylolpropane tri-(norborn-2-ene-5-carboxylate) (TMPTN), and any combinations thereof.

21. A method of preparing a shaped dental prosthetic device for use in a human mouth, the method comprising:
dispensing a photopolymerizable composition comprising:
a. polymerizable monomers, wherein:
about 50% to about 70% of the total weight of the polymerizable monomers is a methacrylate monomer,
the balance by weight of the polymerizable monomers is a mixture of a thiol monomer and an ene monomer; and,
the molar ratio of thiol functional groups from the thiol monomer relative to the ene functional groups from the ene monomer is greater than about 1.5:1;
b. a photoinitiator; and
c. a filler;
shaping the composition into a form of the shaped dental prosthetic device; and
photopolymerizing the shaped composition.

22. The method of claim 21, wherein the molar ratio of the thiol functional groups to the ene functional groups is equal to or greater than about 1.75:1.

23. The method of claim 22, wherein the molar ratio of the thiol functional groups to the ene functional groups is equal to or greater than about 2:1.

* * * * *